United States Patent [19]

Haigwood

[11] Patent Number: 5,817,792
[45] Date of Patent: Oct. 6, 1998

[54] DNA SEQUENCES ENCODING HIV-1 ENVELOPE MUTEINS CONTAINING HYPERVARIABLE DOMAIN DELETIONS

[75] Inventor: Nancy L. Haigwood, Oakland, Calif.

[73] Assignee: Chiron Corporation, Emeryville, Calif.

[21] Appl. No.: 441,356

[22] Filed: May 15, 1995

Related U.S. Application Data

[62] Division of Ser. No. 371,618, Jan. 12, 1995, which is a continuation of Ser. No. 6,252, Jan. 19, 1993, abandoned, which is a continuation of Ser. No. 243,944, Sep. 13, 1988, abandoned.

[51] Int. Cl.$^6$ .......................... C07H 21/04; C07H 21/02; A61K 39/21
[52] U.S. Cl. .................. 536/23.72; 536/23.1; 424/188.1; 424/208.1; 432/435
[58] Field of Search .................................. 435/69.1, 71.1, 435/172.3; 424/188.1, 208.1; 530/350; 536/23.72

[56] References Cited

U.S. PATENT DOCUMENTS

| | | | |
|---|---|---|---|
| 5,128,319 | 7/1992 | Arlinghaus | 514/12 |
| 5,156,949 | 10/1992 | Luciw et al. | 435/5 |

FOREIGN PATENT DOCUMENTS

| | | |
|---|---|---|
| 0187041 | 7/1986 | European Pat. Off. . |
| 0242216 | 10/1987 | European Pat. Off. . |

OTHER PUBLICATIONS

Starcich et al., "Identification and characterization of conserved and variable regions in the envelope gene of HTLV-III/LAV, the retrovirus of AIDS" *Cell* (1986)45:637–648.

Coffin, J.M., "Genetic variation in AIDS viruses" *Cell* (1986)46:1–4.

Modrow et al., "Computer–assisted analysis of envelope protein sequences of seven Human Immnuodeficiency Virus isolates: Prediction of antigenic epitopes in conserved and variable regions" *J. Virol.* (1987)61(2):570–578.

Hahn et al., "Genetic variation of human immunodeficiency virus type–1 in vivo" *Nature* (1988) 334:440–444.

Saag et al., "Extensive variation of human immunodeficiency virus type–1 in vivo" *Nature* (1988) 334:440–444.

Fisher et al., "Biologically diverse molecular variants within a single HIV–1 isolate" *Nature* (1988) 334:444–447.

Rusche et al., "Antibodies that inhibit fusion of human immunodeficiency virus–infected cells bind a 24–amino acid sequence of the viral envelope, gp120" *Proc. Natl. Acad. Sci. USA* (1988) 85:3198–3202.

Looney et al., "Type–restricted neutralization of molecular clones of human immunodeficiency virus" *Science* (1988) 241:357–359.

Goudsmit et al., "Human immunodeficiency virus type 1 neutralization epitope with conserved architecture elicits early type–specific antibodies in experimentally infected chimpanzees" *Proc. Natl. Acad. Sci. USA* (1988) 85:4478–4482.

Koff et al., "Development and testing of AIDS vaccines" *Science* (1988) 241:426–432.

Alizon et al., "Genetic variability of the human and simian AIDS viruses" *Vaccines* 1987 Cold Spring Harbor Laboratory (1987) pp. 146–153.

(List continued on next page.)

*Primary Examiner*—Laurie Scheiner
*Assistant Examiner*—Jeffrey S. Parkin
*Attorney, Agent, or Firm*—Alisa A. Harbin; Dale H. Hoscheit; Robert P. Blackburn

[57] ABSTRACT

HIV-1 envelope muteins are provided comprising deletions within the hypervariable domains of the polypeptides. Methods of using these proteins in immunoassay and to elicit antibody production are also disclosed, as well as materials and methods useful for producing the muteins by recombinant DNA technology.

15 Claims, 59 Drawing Sheets

OTHER PUBLICATIONS

Sternberg et al., "Prediction of antigenic determinants and secondary structures of the major AIDS virus proteins" *FEBS Letters* (1987) 218(2):231–237.

Desai et al., "Molecular cloning and primary nucleotide sequence analysis of a distinct human immunodeficiency virus isolate reveal significant divergence in its genomic sequence" *Proc. Natl. Acad. Sci. USA* (1986) 83:8380–8384.

Gurgo et al., "Envelope Sequences of two new United States HIV–1 isolates" *Virology* (1988) 164:531–536.

Yourno et al., "Nucleotide sequence anaylsis of the env gene of a new zairian isolate of HIV–1" *AIDS Res. and Human Retroviruses* (1988) 43:165–173.

Srinivasan et al., "Molecular characterization of human immunodeficiency virus from Zaire: nucleotide sequence analysis identifies conserved and variable domains in the envelope gene" *Gene* (1987) 52:71–82.

Barr et al., "Antigenicity and immunogenicity of domains of the human immunodeficiency virus (HIV) envelope polypeptide expressed in the yeast *Saccharomyces cerevisiae*" *Vaccine* (1987) 5(2):90–101.

Ho et al., 1987, J. Virol. 61:2024–2028.

Ho et al., 1988, Science 239:1021–1023.

| | | |
|---|---|---|
| HXB2 | MetArgValLysGluLys........TyrGlnHisLeuTrpArgTrpGlyTyrTrpArgTrp | 17 |
| BRU | ————————————————————————————————————Lys——— | 17 |
| MN | ————————GlyIleArgArgAsn————————..———————..— | 16 |
| SC | ————————GlySerGlyArgAsn————————————————————— | 16 |
| SF2 | ————Lys————GlyThrArgArgAsn——————————————————— | 16 |
| NY5 | ————Ala————GlyThrArgLysAsn——————————————————— | 16 |
| CDC4 | ————Ala————GlyIleArgLysAsnCys———————————————— | 16 |
| WMJ2 | ————————GlyIleMetArgAsnCys—————————————————— | 16 |
| RF | ————Met————MetArgLysAsnCys————————Ile———————— | 16 |
| MAL | ————Arg————IleGlnArgAsn——————————AsnTrp—Lys——— | 16 |
| ELI | ————————AlaArgGlyIleGluArgAsnCys——AsnTrp—Lys——— | 16 |
| Z6 | ————AlaArg————IleGluArgAsnCysProAsn————Lys——— | 16 |
| Z3 | ————————IleGlnArgAsn——————————————————Lys——— | 16 |
| Z321 | ————Lys————GlyIleGlnGlyAsnTrp——AsnTrp—Lys——— | 16 |
| JY1 | ————————MetGlyIleArgMetAsn————————————Lys——— | 16 |

FIG. 2-1A

FIG. 2-1B signal peptide \/ gp120
*                    ──► CL

| | GlyThrMetLeuLeuGlyMetLeuMetIleCys | SerAlaThrGluLysLeuTrpValThr | |
|---|---|---|---|
| HXB2 | ──────────────────────────────── | ──────────────────────────── | 37 |
| BRU  | ──────────────────────────────── | ──────────────────────────── | 37 |
| MN   | ─────────────Ile──────────────── | ──────────────────────────── | 36 |
| SC   | ─────────────Leu──────────────── | ──────────────────────────── | 36 |
| SF2  | ─────────────Ile──────────────── | ─────────Ala────Gln───────── | 36 |
| NY5  | ───Leu───────Ile──────────────── | ──────────────────────────── | 36 |
| CDC4 | ─────────────Ile──────────────── | ─────────Ala────Gln───────── | 36 |
| WMJ2 | ─────────────Ile──────────────── | ─────────AlaAlaAsn────────── | 36 |
| RF   | ───Phe───────Trp──────────────── | ─────────Val────Gln───────── | 36 |
| MAL  | ───Met───────Thr──────────────── | ─────────Ala────Asp───────── | 36 |
| ELI  | ─────────────Ile────Thr───────── | ─────────IleAla─Asp───────── | 36 |
| Z6   | ─────────────Ile────Thr───────── | ─────────AlaAspAsn────────── | 36 |
| Z3   | SerLeuIleIle────────Ile───────── | ─────────AlaAspAsn────────── | 36 |
| Z321 | ───LeuIle────LeuValIle────────── | ──Lys────Ile────Ser───────── | 36 |
| JY1  | ─────────────Ile────Thr───────── | ─────────Ala────Asn───────── | 36 |
|      | ─────────────Ile────────ValAla── | ─────────Val────Asp───────── | 36 |

|        | ValTyrTyrGlyValProValTrpLysGluAlaThrThrThrLeuPheCysAlaSerAsp | |
|--------|--------------------------------------------------------------|----|
| HXB2   | * | 57 |
| BRU    | ———————————————————————————————————————————————————————————— | 57 |
| MN     | ———————————————————————————————————————————————————————————— | 56 |
| SC     | ———————————————————————————————————————————————————————————— | 56 |
| SF2    | ———————————————————————————————————————————————————————————— | 56 |
| NY5    | ———————————————————————————————————————————————————————————— | 56 |
| CDC4   | ———————————————————————————————————————————————————————————— | 56 |
| WMJ2   | ———————————————————————————————————————————————————————————— | 56 |
| RF     | ————————————————————————————Glu—————————————————————————————— | 56 |
| MAL    | ———————————————————————————————————————————————————————————— | 56 |
| ELI    | ———————————————————————————————————————————————————————————— | 56 |
| Z6     | ———————————————————————————————————————————————————————————— | 56 |
| Z3     | ——————————Asp———————Glu——————————————————————————————————————— | 56 |
| Z321   | ——————————Asp———————Glu——————————————————————————————————————— | 56 |
| JY1    | ———————————————————————————————————————————————————————————— | 56 |

FIG. 2-2A

| | AlaLysAlaTyrAspThrGluValHisAsnValTrpAlaThrHisAlaCysValProThr | |
|---|---|---|
| HXB2 | | 77 |
| BRU | | 77 |
| MN | ———————————————Gln——————————————— | 76 |
| SC | | 76 |
| SF2 | ———Arg———————————————Ile——————————— | 76 |
| NY5 | | 76 |
| CDC4 | ——————————Ala————————————————————— | 76 |
| WMJ2 | ——————Ser——Ala————————————————————— | 76 |
| RF | ——————Lys——————————Lys——————————— | 76 |
| MAL | ———Ser——Glu——————————Ile——————————— | 76 |
| ELI | ———Ser——Glu——Ala——————Ile——————————— | 76 |
| Z6 | ———Ser——Lys——Ala——————Ile——————————— | 76 |
| Z3 | ——————GluLys——Ser———————————Ser————— | 76 |
| Z321 | ————————Lys——————————————————————— | 76 |
| JY1 | ———Ser——GluPro——Ala——————Ile——————————— | 76 |

|       | AsnAspMetValGluGlnMetHisGluAspIleIleSerLeuTrpAspGlnSerLeuLys |       |
|-------|---|----|
| HXB2  | AsnAspMetValGluGlnMetHisGluAspIleIleSerLeuTrpAspGlnSerLeuLys | 117 |
| BRU   | ———————————————————————————————————— | 117 |
| MN    | ———Asn——————————————————————————————— | 116 |
| SC    | ———Asn——————————————————————————————— | 116 |
| SF2   | ———Asn——————————————————————————————— | 116 |
| NY5   | ———AsnThr————————————————————————————— | 116 |
| CDC4  | ———Asn——————————————————————————————— | 116 |
| WMJ2  | ———Asn——————————————————————————————— | 116 |
| RF    | ———Asn——————————————————————————————— | 116 |
| MAL   | ———Asn——————————————————————————————— | 116 |
| ELI   | ———Asn——————————————————————————————— | 116 |
| Z6    | ———Asn——————————————Ile——————————————— | 116 |
| Z3    | ———Lys——————————————————————————————— | 116 |
| Z321  | ———Asn——————————————————Val—————————— | 116 |
| JY1   | ———Asn——————————————————————————Asn——— | 116 |

FIG. 2-3A

| | | | | |
|---|---|---|---|---|
| HXB2 | ProCysValLysLeuThrProLeuCysValSerLeuLysCys | ThrAspLeuLys...... | 135 |
| BRU | | Gly | 135 |
| MN | Thr—Asn | Arg | 134 |
| SC | Thr—Asn | Asn—Arg | 134 |
| SF2 | Thr—Asn | GlyLys | 135 |
| NY5 | Ser—Thr—Asn | Thr | 134 |
| CDC4 | Thr—Asn | AsnThr | 135 |
| WMJ2 | Thr—Asn | Ile—Lys... | 133 |
| RF | Thr—Asn | Ala/AsnLeu | 135 |
| MAL | Thr—Asn—AsnVal... | | 133 |
| ELI | Thr—Asn | Ser—GluLeuArg | 135 |
| Z6 | Thr—Asn | GluSerAspGlu | 136 |
| Z3 | Phe—Thr—Asn | Ile—Val | 134 |
| Z321 | Thr—Ser | HisAsnIleThrIleLys | 136 |
| JY1 | Thr—Asn | AsnAlaGlyGly | 135 |

FIG. 2-3B

| | | | | |
|---|---|---|---|---|
| HXB2 | ......AsnAspThr...AsnThrAsnSerSer... | [ ] | ......AsnThrAsnSerSer......Ser | 144 |
| BRU | ———Ala——— | ——— | ———AsnThrAsnSerSer——— | 149 |
| MN | ———Thr——— | ———Asn——— | ThrAlaAsnAsnAsn——— | 148 |
| SC | ——— | ———Ser——— | ———AsnThrThrSerSerAsn | 148 |
| SF2 | ...Ala——— | ———AlaThr——— | ———AsnTrpLys——— | 145 |
| NY5 | ———Ala——— | ———TyrAla...———Gly——— | ——— | 142 |
| CDC4 | ———Asn——— | ———...——— | ThrThrGluLeuSerIleIleValVal... | 149 |
| WMJ2 | ———Ile——— | ———AspTrpLys———ThrThr——— | ———IleIle——— | 144 |
| RF | ——— | ———Gly———......——— | ———ValThr——— | 144 |
| MAL | ——— | ———Gly———AlaVal...——— | ———SerSer——— | 149 |
| ELI | ———Asn———Gly———MetGlyAsn——— | ———GlyThrAsnAlaGlySerAsnArgThrAsn | 145 |
| Z6 | TrpMetGly———Val———GlyLys...——— | ———ValThr——— | ——— | 147 |
| Z3 | ——— | ———...——— | ———AsnThr——— | 141 |
| Z321 | Asp——— | ———...ValAspThr——— | ——— | 144 |
| JY1 | ———Lys———Thr———Gly———AsnThr——— | ———ThrAsnGln——— | 147 |

| | | D1 → | ← D2 | | |
|---|---|---|---|---|---|
| HXB2 | GlyArgMetIleMetGluLys...GlyGlyIleLysAsn | Cys | SerPheAsnIleSerThr | ] | 163 |
| BRU | ---Glu---Met--- | --- | --- | --- | 168 |
| MN | AsnSerGluGlyThrIle---Gly--- | --- | ---Thr--- | --- | 168 |
| SC | ArgGly...Lys---Gly--- | --- | ---Thr--- | --- | 166 |
| SF2 | .....GluGlu...Ile---MetThr--- | --- | ---Thr--- | --- | 161 |
| NY5 | ...SerGluGluArg.........---Arg--- | --- | ---ValThr--- | --- | 158 |
| CDC4 | ...TrpGluGlnArgGly---MetArg--- | --- | ---Thr--- | --- | 167 |
| WMJ2 | ...........GlyGly---Val--- | --- | ---Thr--- | --- | 158 |
| RF | ---GlyThrMet---Asn--- | --- | ---GlnValThr--- | --- | 163 |
| MAL | AlaGluLeuLys---Ile---Val--- | --- | ---ThrPro--- | --- | 168 |
| ELI | ...ThrGluGlu......---Gly---Met--- | --- | ---ValThr--- | --- | 160 |
| Z6 | ...GluAspIleArg......---Met--- | --- | ---Thr--- | --- | 161 |
| Z3 | ...GluGluAlaThr............---Thr--- | --- | ---LysValPro--- | --- | 155 |
| Z321 | ............GluMet---Glu--- | --- | --- | --- | 159 |
| JY1 | GluGluGlnMet---Met--- | --- | ---Tyr---MetThr--- | --- | 166 |

FIG. 2-4A

| | | | | | | | | | | | |
|---|---|---|---|---|---|---|---|---|---|---|---|
| HXB2 | SerIleArgGlyLysValGlnLysGluTyrAlaPhePheTyrLysLeuAspIleIlePro | | | | | | | | | | 183 |
| BRU | — | | | | | | | | | | 188 |
| MN | —Asp—Met— | | | | | | | LeuLeu— | | ValSer— | 188 |
| SC | —Ser— | | | | | | | Leu— | | ValVal— | 186 |
| SF2 | —Asp—Ile— | | | | | Asn— | | Leu— | ArgAsn— | ValVal— | 181 |
| NY5 | Ile—Asn—Ile— | | | | | | | Leu— | Arg— | Val— | 178 |
| CDC4 | —Asp— | | | | Arg— | | | Leu— | | ValGlu— | 187 |
| WMJ2 | —Arg—Asp— | | | His— | | | | Leu— | | ValVal— | 178 |
| RF | —Arg—Asp—Thr— | | | | | Lys— | | Leu— | | ValVal— | 183 |
| MAL | ValGlySerAsp—Arg— | | ... — | | | | | Thr— | | LeuValGln— | 187 |
| ELI | ValLeuLysAsp—Lys— | | GlnVal— | | | | | Leu— | | Val— | 188 |
| Z6 | ValVal—Asp— | | ThrLysGlnValHis— | | | | | Leu— | Arg— | Val— | 181 |
| Z3 | GluLeuLysAsp— | | ThrGluThrValHisThrLeu— | | | | | | Arg— | ValVal— | 175 |
| Z321 | GluLeu—Asp— | | GlnArg—Ile— | | | | | SerLeu— | Arg— | Val— | 179 |
| JY1 | Val—SerAsp— | | LysLysGlnValHis— | | | | | Leu— | Arg— | ValVal— | 186 |

FIG. 2-4B

```
                          [              ]   "peptide T" region
HXB2   Ile..............AspAsnAspThr............Thr                          189
BRU    ─────────────────────────────────────────────                         194
MN     ─────────────Ser─────────────────────────────                         194
SC     ─────────────...─────────────────────────────                         190
SF2    ─────────────AlaSer──────────ThrThrThrAsnTyr──                        192
NY5    ─────AspLys──...─────────────────────────────                         184
CDC4   ─────Asp─────LysAsn──────────ThrThrAsnAsn────                         198
WMJ2   ─────LysGly──AsnSer──────────────────────Ser─                         186
RF     ─────GluLysGly...────IleSerProLysAsnAsnThrSerAsnAsn──                 199
MAL    ───AspAspSer─────────Ser──────────────────Ser                         194
ELI    ─────────────Ser──────────────SerThrAsnSer───                         190
Z6     ─────────────Asn──────────────SerThrAsnSer───                         191
Z3     Leu──...─────Val─────AsnAsnSerSerIleSer───Ser                         186
Z321   ───GlyGly────...─────SerSerAsnGlyAspSerSer────                        190
JY1    ───AspAspAsnSerAla...ThrSer──Asn──────────ThrAsnTyr──                 201
```

FIG. 2-4C

| | LysValSerPheGluProIleProIleHisTyrCysAlaProAlaGlyPheAlaIleLeu | |
|---|---|---|
| HXB2 | * | 226 |
| BRU | ———————————————————————————————— | 231 |
| MN | ——Ile———————————————————————————— | 231 |
| SC | ———————————————————————————————— | 226 |
| SF2 | ————————————————————ArgTrp.... | 229 |
| NY5 | ————————Thr—————————————————— | 221 |
| CDC4 | ———————————————————————————————— | 235 |
| WMJ2 | ————————Thr——Thr————Leu———— | 223 |
| RF | ————————————————Thr———————— | 239 |
| MAL | ——Thr—Asp——————————————————— | 231 |
| ELI | ———————————————————————————————— | 227 |
| Z6 | ———————————————————————————————— | 228 |
| Z3 | ———————————————————————————————— | 223 |
| Z321 | ———————————————————————————————— | 227 |
| JY1 | ————————Thr——————————————— | 238 |

FIG. 2-5B

|       |   * | [ |   |   |   | ] | [ |   |   |   |   |   |   |   |   |   |   |   | ] | * | [ |   |   |   |   | ] |     |
|-------|-----|---|---|---|---|---|---|---|---|---|---|---|---|---|---|---|---|---|---|---|---|---|---|---|---|---|-----|
| HXB2  | Lys Cys Asn Asn Lys Thr Phe Asn Gly Thr Gly Pro Cys Thr Asn Val Ser Thr Val Gln | | | | | | | | | | | | | | | | | | | | | | | | | | 246 |
| BRU   | ———————————————————————————————————————————————————————————————————————— | | | | | | | | | | | | | | | | | | | | | | | | | | 251 |
| MN    | ———Asp———Lys———Ser———Lys———Ser———Lys———————————————————————————————— | | | | | | | | | | | | | | | | | | | | | | | | | | 251 |
| SC    | ——Asn———————————Lys———————Lys——————————————————————————————————————— | | | | | | | | | | | | | | | | | | | | | | | | | | 246 |
| SF2   | ———————————————————————Lys——————————————————————————————————————————— | | | | | | | | | | | | | | | | | | | | | | | | | | 249 |
| NY5   | ———Asp———Lys——————————————————————————————————————————————————————— | | | | | | | | | | | | | | | | | | | | | | | | | | 241 |
| CDC4  | ———Asp———Lys——————————————————————————————————————————————————————— | | | | | | | | | | | | | | | | | | | | | | | | | | 255 |
| WMJ2  | ———Asp———Lys——————————————————————————————————————————————————————— | | | | | | | | | | | | | | | | | | | | | | | | | | 243 |
| RF    | ———Asp———Lys———————————————————————————Lys———————————————————————— | | | | | | | | | | | | | | | | | | | | | | | | | | 259 |
| MAL   | ———Asp———Lys———————————————————————GluIle———Lys————————————————— | | | | | | | | | | | | | | | | | | | | | | | | | | 251 |
| ELI   | ——ArgAsp———Lys——————————————————————————————————————————————————— | | | | | | | | | | | | | | | | | | | | | | | | | | 247 |
| Z6    | ——ArgAsp———Arg——————————————————————————————————————————————————— | | | | | | | | | | | | | | | | | | | | | | | | | | 248 |
| Z3    | ———Asp———Lys———————————————————————————Lys———————————————————————— | | | | | | | | | | | | | | | | | | | | | | | | | | 243 |
| Z321  | ——ArgAspGluGlu———Lys———————————————————Arg———————————————————————— | | | | | | | | | | | | | | | | | | | | | | | | | | 247 |
| JY1   | ——LysAsp———Lys———————————————————————LysLys—————————————————————— | | | | | | | | | | | | | | | | | | | | | | | | | | 258 |

FIG. 2-5C

|        | * CysThrHisGlyIleArgProValValSerThrGlnIleLeuLeuLeuAsnGlyGlySerLeuAla | |
|--------|---|---|
| HXB2   |   | 266 |
| BRU    | ---------------------------------------------------- | 271 |
| MN     | ---------------------------------------------------- | 271 |
| SC     | ---------------------------------------------------- | 266 |
| SF2    | ----------------His--------------------------------- | 269 |
| NY5    | ---------Ile---------------------------------------- | 261 |
| CDC4   | ------Lys------------------------------------------- | 275 |
| WMJ2   | ---------------------------------------------------- | 263 |
| RF     | ---------------------------------------------------- | 279 |
| MAL    | ---------------------------------------------------- | 271 |
| ELI    | ------Lys------------------------------------------- | 267 |
| Z6     | ---------------------------------------------------- | 268 |
| Z3     | ---------------------------------------Ser---------- | 263 |
| Z321   | ---------------------------------------------------- | 267 |
| JY1    | ---------------------------------------------------- | 278 |

FIG. 2-6A

| | | | | | | | | | | | | |
|---|---|---|---|---|---|---|---|---|---|---|---|---|
| HXB2 | GluGluGluValValIleArgSerVal | Asn | Phe | Thr | Asp | Asn | Ala | Lys | Thr | Ile | IleVal | 286 |
| BRU  | — | — | — | — | — | Ala | — | — | — | — | — | 291 |
| MN   | — | — | — | — | — | Glu | — | — | — | — | — | 291 |
| SC   | — | Leu | — | — | — | Glu | — | — | — | — | — | 286 |
| SF2  | — | — | — | Asp | — | Asn | — | — | — | — | — | 289 |
| NY5  | —Gly— | — | — | — | — | Glu | — | — | — | — | — | 281 |
| CDC4 | — | — | — | — | — | Glu | — | — | — | — | — | 295 |
| WMJ2 | —Ile— | — | — | — | — | Asn | — | — | — | — | — | 283 |
| RF   | — | — | — | — | — | Glu | — | — | Val | — | — | 299 |
| MAL  | IleMet | — | — | — | — | Glu | Leu | — | Thr | Asn | — | 291 |
| ELI  | —Ile— | — | — | — | — | Glu | Leu | Asn | — | Asn | Ala | 287 |
| Z6   | —IleIle | — | — | — | — | Glu | Leu | Asn | — | Ile | — | 288 |
| Z3   | —Ile— | — | — | — | — | Glu | Ile | Asn | — | — | — | 283 |
| Z321 | —Arg— | — | — | — | — | Glu | — | — | Ile | — | — | 287 |
| JY1  | —IleIle | — | — | — | — | Glu | Leu | Asn | — | — | Val | 298 |

FIG. 2-6B

|        |                                                                          |     |
|--------|--------------------------------------------------------------------------|-----|
| HXB2   | Arg......IleArgIleGlnArgGlyProGlyArgAlaPheValThrIleGlyLys                | 322 |
| BRU    | Ser——————————————————————————————————————————————————                    | 327 |
| MN     | ——————His—————————————————————————————————Tyr———ThrLysAsn                | 325 |
| SC     | Ser—————His———————————————————————————————TyrAlaThr———Asp                | 329 |
| SF2    | Ser—————Tyr———————————————————————————————His———Thr———Arg                | 323 |
| NY5    | Gly—————Ala———————————————————————————————————————————                   | 315 |
| CDC4   | ————ValThrLeu..———————————————————————ThrLeuTyrAlaArgGlu——               | 329 |
| WMJ2   | Ser—————LeuSer———————————————————————————ValTrpTyr———Thr———Glu           | 316 |
| RF     | Ser—————ThrLys———————————————————————————Arg...Arg...Glu                 | 333 |
| MAL    | Gly—————HisPhe———————————————————————ValIleTyrAlaThr———Gln               | 324 |
| ELI    | ————————ThrPro———————————————————————Gln———LeuTyr———Thr———..             | 321 |
| Z6     | ————————ThrPro———————————————————Leu—GlnSerLeuTyr———ThrArgSer            | 322 |
| Z3     | Ser—————GlnSer—ArgIle————————————————Leu—Gln—LeuTyr———ThrArgGly          | 319 |
| Z321   | Ser—————Ser—————————————————————————LysVal—TyrAlaLys———Gly               | 321 |
| JY1    | Ser—————ThrPro———————————————————————PheAlaThr———Asp                     | 332 |
|        |                                                                          |     |
|        | ———————————————————————Leu—Gln—LeuTyr———ThrArg...                        |     |

FIG. 2-7A

|       |                              |     |
|-------|------------------------------|-----|
| HXB2  | ...IleGlyAsnMetArgGlnAlaHisCysAsnIleSerArgAlaAlaLysTrp | 338 |
| BRU   | ———————————————————————————— | 343 |
| MN    | ————Ile————ThrIle———————————— | 342 |
| SC    | ————Ile————AspIle———————————— | 337 |
| SF2   | ————Ile————AspIle————Lys—————— | 340 |
| NY5   | ————Ile————AspIle———————————— | 332 |
| CDC4  | ————Ile————IleLeu————————Lys——Gln—— | 346 |
| WMJ2  | ————Ile————IleIle———————————Gln—— | 333 |
| RF    | ————Ile————AspIle————Lys————Leu——Gln—— | 350 |
| MAL   | ————IleVal————AspIle————Arg————Thr——AsnGluThrGlu—— | 341 |
| ELI   | Arg——SerIle............————Tyr——————Gln—— | 337 |
| Z6    | ArgThrLysIle............——————————LysGluAsp—— | 339 |
| Z3    | ————IleThr............——————————ThrAspGlyGlu—— | 333 |
| Z321  | ————Ile————AspIle——————————Val————ThrGlu—— | 338 |
| JY1   | ————IleLys————AspIle————Tyr——————Ala————Ala—— | 349 |

FIG. 2-7B

|       |   |   |                                         |     |
|-------|---|---|-----------------------------------------|-----|
| HXB2  | [ | ] | AsnAsnThrLeuLysGlnIleAspSerLysLeuArgGluGlnPheGlyAsnAsn...Lys | 357 |
| BRU   |   |   | ——Ala——————————————————————————————————— | 362 |
| MN    |   |   | ——Asp——————Arg———————————Val——————Lys——————————— | 360 |
| SC    |   |   | ————————————————ValIle——————Asp——Glu——...——— | 355 |
| SF2   |   |   | ——————————————————ValLys———————————————————— | 359 |
| NY5   |   |   | ——Asp——————————————ValThr—————Lys——————...——— | 350 |
| CDC4  |   |   | ——————————Gln——————AlaThrThr——————————Arg——...——— | 364 |
| WMJ2  |   |   | ————————————————ValGlu———————————Lys——...——— | 351 |
| RF    |   |   | ——————————————ValValThr———————————Asp——...——— | 368 |
| MAL   |   | AspLys————————ValAlaVal————GlySerLeuLeuAsnLysThr——... | 359 |
| ELI   |   | SerLys————————ValAlaArg————GlyThrLeuLeuAsnLysThr——... | 355 |
| Z6    |   | ——Lys————GlnArgValAlaIle————GlyAsnLeuLeuAsnLysThr——... | 357 |
| Z3    |   | Arg——————————ValAlaIleAla————Arg——————Asn——...——— | 351 |
| Z321  |   | ——Asp————SerLysValAlaAlaGln————LysHis——Val——ThrSerThr | 358 |
| JY1   |   | ——Lys————————Gln————ValAlaLys————GlyAspLeuLeuAsnGlnThr——... | 367 |

FIG. 2-7C

| | | | | | | | | | | | | | | | | | | |
|---|---|---|---|---|---|---|---|---|---|---|---|---|---|---|---|---|---|---|
| HXB2 | ] → C3 | Thr | Ile | Ile | Phe | Lys | Gln | Ser | Ser | Gly | Gly | Asp | Pro | Glu | Ile | Val | Thr | His | Ser | Phe | Asn | 377 |
| BRU | | --- | --- | --- | --- | --- | --- | --- | --- | --- | --- | --- | --- | --- | --- | --- | --- | --- | --- | --- | --- | 382 |
| MN | | --- | --- | --- | --- | --- | Val | --- | --- | --- | --- | Asn | --- | --- | --- | --- | --- | --- | --- | --- | Met | --- | 380 |
| SC | | --- | --- | --- | --- | --- | --- | --- | --- | --- | --- | Asn | Arg | --- | --- | --- | --- | --- | --- | --- | Met | --- | 375 |
| SF2 | | --- | --- | --- | --- | --- | Val | --- | --- | --- | --- | Asn | --- | --- | --- | --- | --- | --- | --- | --- | Met | --- | 379 |
| NY5 | | --- | --- | --- | --- | --- | Val | --- | --- | --- | --- | Asn | --- | --- | --- | --- | --- | --- | --- | --- | Met | --- | 370 |
| CDC4 | | --- | --- | --- | --- | --- | Ala | --- | --- | --- | --- | Asn | --- | --- | --- | --- | --- | --- | --- | --- | Met | --- | 384 |
| WMJ2 | | --- | --- | --- | --- | --- | Val | --- | --- | --- | --- | Asn | His | --- | --- | --- | --- | --- | --- | --- | --- | --- | 371 |
| RF | | --- | --- | --- | --- | --- | Val | --- | --- | Thr | Ser | --- | --- | --- | --- | --- | --- | --- | --- | --- | Leu | --- | 388 |
| MAL | | --- | --- | --- | --- | --- | Lys | --- | --- | Asn | Ser | --- | --- | --- | --- | --- | --- | --- | --- | --- | Thr | --- | 379 |
| ELI | | --- | --- | --- | --- | --- | Ile | --- | Lys | --- | --- | Pro | --- | --- | --- | --- | --- | --- | --- | --- | Thr | --- | 375 |
| Z6 | | --- | --- | --- | --- | --- | --- | --- | --- | --- | --- | Pro | --- | --- | --- | Ala | --- | --- | --- | --- | Thr | --- | 377 |
| Z3 | | --- | --- | --- | --- | --- | Ser | --- | --- | Asn | Ser | --- | --- | --- | --- | Ile | --- | --- | --- | Thr | Thr | --- | 371 |
| Z321 | | --- | --- | --- | --- | --- | Asp | --- | --- | Ala | Asn | --- | --- | --- | --- | Val | --- | --- | --- | --- | Thr | --- | 378 |
| JY1 | | --- | --- | --- | --- | --- | --- | --- | --- | --- | --- | Pro | Pro | Ala | --- | --- | --- | --- | --- | --- | Thr | --- | 387 |

FIG. 2-8A

|  |  | C3 → D4 |  |  |
|---|---|---|---|---|
| HXB2 | * | CysGlyGlyGluPhePheTyrCys[AsnSerThrGlnLeuPheAsnSerThrTrp......] | 395 |
| BRU  |   | ------------------------------------------------------------- | 400 |
| MN   |   | -------------------------------ThrSerPro-------------------- | 398 |
| SC   |   | -------------------------------------Ser-------------------- | 393 |
| SF2  |   | ---Arg--------------------------Thr-----Asn----------------- | 397 |
| NY5  |   | -------------------------------LysThr----------------------- | 388 |
| CDC4 |   | -----------------------------------------Ala----Asn--------- | 403 |
| WMJ2 |   | ------------------------------------------------------------- | 389 |
| RF   |   | -------------------------------Thr-------------------------- | 406 |
| MAL  |   | ---Arg--------------------------ThrSerLys------------------- | 397 |
| ELI  |   | -------------------------------ThrSerGly-------------------- | 393 |
| Z6   |   | -------------------------------ThrSerGly-------------------- | 395 |
| Z3   |   | -------------------------------ThrSerGlu-------ThrGlyIle---- | 389 |
| Z321 |   | -------------------------------ThrSerGly----------Gly--LeuAsn | 398 |
| JY1  |   | -------------------------------ThrSerArg-------------------- | 405 |

FIG. 2-8B

```
                [            ]                          [                    ]
HXB2   .....PheAsnSerThr...TrpSerThr.........GluGlySerAsnAsnThrGlu            409
BRU    ─────────────────────────────────────────────────────────────          414
MN     ─────AsnGly────Asn─────────AsnAsnThr─────────────Asn...                413
SC     ──────...─────Gly──────────────────────────────────────Gly─────        403
SF2    ─────ArgLeu────His─────────────────────────────────────Lys────         406
NY5    ─────Leu───────────────────AsnAsp──────────Thr─────Arg────...Asp──     401
CDC4   ValThrSer────Gly───────────...────────────Thr─────Arg────ValThrArgLys  415
WMJ2   ──...─────Gly────Asp─────────...────────────────────────...           400
RF     ──...─────────────────────────...────────────IleLys────Asp───LysAsn... 416
MAL    ─────GlnAsn────GlyAlaArg.........................Leu────Ser────Gly     409
ELI    ─────...────IleSerAla─────AsnAsnIleThr──...Glu────SerThr────           408
Z6     ─────AsnIle────AsnSer────────────────────────────Ala────Ser────        407
Z3     ──...─────Gly────────────AspLysAsnCys─────────...ThrSer────            401
Z321   GlyThrSer────Asn─────────LysIleAspThr─────────...────────             409
JY1    ──...────────SerThr─────AsnAsnAspThr─────────...Leu────Ser────         418
```

FIG. 2-8C

```
              --- CD4 binding region ---                        *
HXB2   TrpGlnLysValGlyLysAlaMetTyrAlaProProIleSerGlyGlnIleArgCysSer    446
BRU    ------Glu-------------------------------------------------------  451
MN     ------Glu--------------------------------Glu--------------------  446
SC     ------Glu--------------------------------Lys------ValLys------   440
SF2    ------Glu--------------------------------Gly---------Ser------   443
NY5    GlyArg---+++                                                     422
CDC4   ------Val---------------------Leu------Lys---Leu-------------   455
WMJ2   ------Gly--------------------------------Gln--------------------  436
RF     ------Glu-------------------------------------------Lys---Ile   453
MAL    ---------Thr-----------------------------Ala---Val---Asn---Leu   446
ELI    ValAlaGlyArg...------Ile-----------------GluArgAsn---Leu-------   443
Z6     ------Gly--------------------------------Glu---------Asn------   445
Z3     ------Gly------Gln-----------------------Glu---Thr-------------   440
Z321   ------Arg------Gln-----------------------Lys---Val---Lys---Val   446
JY1    ------Gly--------------------------------Glu---Leu---Lys---Thr   453
```

FIG. 2-9B

```
         [                    ]                                        C4 →   ← D5
HXB2   SerAsnIleThrGlyLeuLeuThrArgAspGlyGly..............AsnSer  461
BRU    -----------------------------------------------------Asn  466
MN     ----------------------------------------------LysAspThrAsp  463
SC     -------------------------------------AsnSerLysAsnGlySerLys  460
SF2    --------------------------------------------------Thr---Val  459
NY5
CDC4   ----------------------------------------Gly---------...Glu  470
WMJ2   ------------------------------------AsnSer---------........  451
RF     --------------------------------------------------GluAspThr  469
MAL    ---------------------------Ile------AsnSer---------SerAsp    463
ELI    ---------------------------------------------------IleAsn    458
Z6     ---------------------------------------------------ThrAsn    460
Z3     -------------------------------AsnGlyLysCysAsnSerLys         460
Z321   ----------------------------VolGly-----------------...Asn    461
JY1    ---------------------------Ile-Val-----------------...Asn    468
```

FIG. 2-9C

| | | D5 → ← C5 | | |
|---|---|---|---|---|
| HXB2 | [ ] | AsnAsnGluSerGluIlePheArgLeuGlyGlyGlyAspMetArgAspAsnTrpArgSer | | 481 |
| BRU | | ---Gly--- | ---Pro--- | 486 |
| MN | Thr---AspThr | | ---Pro--- | 483 |
| SC | ---GluAsnThr | | ---Pro--- | 480 |
| SF2 | Thr---AspThr | ---Val--- | ---Pro--- | 479 |
| NY5 | | | | |
| CDC4 | ---GlnThrThr | | ---Pro--- | 490 |
| WMJ2 | SerSerArgGlu | | ---Pro---Asn--- | 471 |
| RF | Thr---ThrThr | | ---Pro---Asn--- | 489 |
| MAL | ---SerAspAsn---ThrLeu | ---Ile--- | ---Pro--- | 483 |
| ELI | ---SerThrAsn---Thr | | ---Pro--- | 478 |
| Z6 | ---SerSerAsn---Thr | | ---Pro--- | 480 |
| Z3 | +++ | | | 461 |
| Z321 | ---ThrSerAsn---Thr | | ---Pro---Lys--- | 481 |
| JY1 | ---SerThrAsn---Thr | ---Asn--- | ---Pro--- | 488 |

FIG. 2-10A

|       | GluLeuTyrLysTyrLysValValLysIleGluProLeuGlyValAlaProThrLysAla |      |
|-------|---|------|
| HXB2  |                                                              | 501  |
| BRU   | ———————————————————————————————————————————————————————————— | 506  |
| MN    | ————————————————————Thr————————————————————————————————————— | 503  |
| SC    | ———————————————————————————————————————————————————————————— | 500  |
| SF2   | ————————————————————————————Ile————————————————————————————— | 499  |
| NY5   | ———————————————————————————————————————————————————————————— |      |
| CDC4  | ————————————————————————————————————Arg————————————————————— | 510  |
| WMJ2  | ————————————————————————————————————Arg————————————————————— | 491  |
| RF    | ————————————————————————————————————Arg——————————Arg———————— | 509  |
| MAL   | ————————————————————————————————————Arg————————————————————— | 503  |
| ELI   | ————————————————————————————————————Gln——————————Arg———————— | 498  |
| Z6    | ———————————————————————————————————————————————————————————— | 500  |
| Z3    | ———————————————————————————————————————————————————————————— |      |
| Z321  | ————————————————————————————————————Arg————————————————————— | 501  |
| JY1   | ————————————————————————————Ile——————————————————Arg———————— | 508  |

FIG. 2-10B

|  | gp120 C5 → | ← gp160 C5 (TO END) | |
|---|---|---|---|
|  | gp120 ∨ gp41 | | |
|  | LysArgArgValValGlnArgGluLysArgAlaValGly...IleGlyAlaLeuPheLeu | | |
| HXB2 | | | 520 |
| BRU | --------------------------------------------------------- | | 525 |
| MN | --------------------------------------------------------- | | 521 |
| SC | ----------------------------------------Ala...----------- | | 520 |
| SF2 | ------------------------------------------------Thr----Met------ | | 519 |
| NY5 | ---------------------------------------------IleVal----Met------ | | |
| CDC4 | -----------------------------------------------MetLeu----Met------ | | 530 |
| WMJ2 | ------------------------------------------------Thr----Met------ | | 511 |
| RF | ------------------------------------------------Thr----Met------ | | 529 |
| MAL | --------------Glu----------------------------------Ile----Leu----Met------ | | 522 |
| ELI | --------------Glu----------------------------------Ile----Leu----Met------ | | 517 |
| Z6 | --------------Glu----------------------------------Ile----Leu----Met------ | | 519 |
| Z3 | | | |
| Z321 | --------------Ala----------------------------------Ile----Met...----Phe------ | | 520 |
| JY1 | --------------Glu----------------------------------Ile----Leu----Val------ | | 527 |

FIG. 2-10C

| | | |
|---|---|---|
| HXB2 | GlyPheLeuGlyAlaAlaGlySerThrMetGlyAlaAlaSerMetThrLeuThrValGln | 540 |
| BRU | ---------------------------------------Arg---------------- | 545 |
| MN | ---------------------------------------------------------- | 541 |
| SC | ---------------------------------------------Val---------- | 540 |
| SF2 | ------------------------------------Thr------------------- | 539 |
| NY5 | ---------------------------------------------Val---Leu---- | |
| CDC4 | ---------------------------------Thr------Ala------------- | 550 |
| WMJ2 | ---------------------------------------Gly---Leu---------- | 531 |
| RF | ---------------------------------------Gly---Ile---------- | 549 |
| MAL | ------------------------------------------------Leu------- | 542 |
| ELI | ---------------------------------------------Arg---Val---- | 537 |
| Z6 | ---------------------------------------------------Val---- | 539 |
| Z3 | ---------------------------------------------------------- | |
| Z321 | ---------------------------------------------Ile---------- | 540 |
| JY1 | ----------------------------------------Val---ValAla------Gly---- | 547 |

FIG. 2-11A

| | | |
|---|---|---|
| HXB2 | AlaArgGlnLeuLeuSerGlyIleValGlnGlnGlnAsnAsnLeuLeuArgAlaIleGlu | 560 |
| BRU | ------------------------------------------------------------ | 565 |
| MN | -------Leu-------------------------------------------------- | 561 |
| SC | -------Leu-------------------------------------------------- | 560 |
| SF2 | ------------------------------------------------------------ | 559 |
| NY5 | ------------------------------------------------------------ | |
| CDC4 | ----------------------------------------------------Lys----- | 570 |
| WMJ2 | -----------------------------------------------------Asp---- | 551 |
| RF | -------His-------------------------------------------------- | 569 |
| MAL | ------------------------------------------------------------ | 562 |
| ELI | ----------Met----------------------------------------------- | 557 |
| Z6 | ----------Met----------------------------------------------- | 559 |
| Z3 | ------------------------------------------------------------ | |
| Z321 | ------Arg--------------------------------------------------- | 560 |
| JY1 | ------------------------------------------------------------ | 567 |

FIG. 2-11B

| | | |
|---|---|---|
| HXB2 | AlaGlnGlnHisLeuLeuGlnLeuThrValTrpGlyIleLysGlnLeuGlnAlaArgIle | 580 |
| BRU | ------------------------------------------------------------ | 585 |
| MN | ----------Met-----------------------------------------Val--- | 581 |
| SC | -------------------------------------------------------Val-- | 580 |
| SF2 | -------------------------------------------------------Val-- | 579 |
| NY5 | | |
| CDC4 | -------------------------------------------------------Val-- | 590 |
| WMJ2 | -------------------------------------------------------Val-- | 571 |
| RF | -------------------------------------------------------Val-- | 589 |
| MAL | -------------------------------------------------------Val-- | 582 |
| ELI | ------------------------------------------------------------ | 577 |
| Z6 | ------------------------------------------------------------ | 579 |
| Z3 | | |
| Z321 | -----------------------------------------Lys--------------- | 580 |
| JY1 | ----------Met------------------------------------------Val-- | 587 |

FIG. 2-11C

```
        HXB2  LeuAlaValGluArgTyrLeuLysAspGlnGlnLeuLeuGlyIleTrpGlyCysSerGly              600
        BRU   ------------------------------------------------------------              605
        MN    ------------------------------------------------------------              601
        SC    ---------------Arg------------------------------------------              600
        SF2   ---------------Arg---------Phe------------------------------              599
        NY5   ------------------------------------------------------------
        CDC4  ---------------------------Phe------------------------------              610
        WMJ2  ---------------Arg------------------------------------------              591
        RF    ---------------Arg------------------------------------------              609
        MAL   ---------------Gln------Met---------------------------------              602
        ELI   ------------------------------------------------------------              597
        Z6    ------------------------------------------------------------              599
        Z3    ------------------------------------------------------------
        Z321  ------------------------------------------------------------              600
        JY1   ---------------Ser------------------------------------------              607
```

FIG. 2-12A

| | | | | | |
|---|---|---|---|---|---|
| HXB2 | * LysLeuIleCysThrThrAlaValProTrpAsnAlaSerTrpSerAsnLysSerLeuGlu | | [ ] | | 620 |
| BRU | ———————————————————————————————————————————————————————————— | | | | 625 |
| MN | ————————————————————Thr——————————————————————————————————Asp | | | | 621 |
| SC | ————————————————————Thr——————————Thr——————————————————————Asp | | | | 620 |
| SF2 | ———————————————————————————————————————————————————————————— | | | | 619 |
| NY5 | ———————————————————————————————————————————————————————————— | | | | |
| CDC4 | ————————————————————Thr——————————————————————————Thr——————Asp | | | | 630 |
| WMJ2 | ————————————————————Thr——————————————————MN 611 | | | | |
| RF | ————————————————————Thr——————————————————————————————————Asn | | | | 629 |
| MAL | ———————————————His——Phe——————————————Ser——————————————————Asp | | | | 622 |
| ELI | ———————————————His——Asn——————————————Ser——————————————————Asn | | | | 617 |
| Z6 | ————————————————————Thr——————————————Ser——————————————————Asn | | | | 619 |
| Z3 | | | | | |
| Z321 | ——————Ile——Pro——Asn——————————————————Ser——————————————GlnSer | | | | 620 |
| JY1 | ——————His——————————Thr——————————————Ser——————————————————————— | | | | 627 |

FIG. 2-12B

| Strain | | | | Position |
|---|---|---|---|---|
| HXB2 | GlnIleTrpAsnHisThrThrTrpMetGluTrpAspArgGluIleAsnAsnTyrThrSer | | | 640 |
| BRU | ———AsnMet——— | | | 645 |
| MN | Asp———AsnMet——— | Gln———Glu——— | Asp——— | 641 |
| SC | Lys———GlyAsnMet——— | ———Glu——— | Asp——— | 640 |
| SF2 | Asp———AspAsnMet——— | Gln———Glu——— | Asp———Asn | 639 |
| NY5 | | | | |
| CDC4 | ———AsnMet——— | ———Asp——— | ———His | 650 |
| WMJ2 | ———AspAsnLeu——— | ———Glu——— | Asp——— | 631 |
| RF | Met———AsnMet——— | Gln———Glu——— | Asp———Gly | 649 |
| MAL | Asp———AsnMet——— | Gln———GluLys——— | Ser———Gly | 642 |
| ELI | Glu———GlnAsnMet——— | ———Glu——— | Asp———Gly | 637 |
| Z6 | Asp———GlnAsnMet——— | ———Glu——— | Asp———Gly | 639 |
| Z3 | | | | |
| Z321 | Asp———AspLysMet———Leu——— | Lys———ValSer——— | ———Gln | 640 |
| JY1 | Glu———AsnMet———Ile——— | Glu——— | Asp———Gly | 647 |

FIG. 2-12C

| | | | |
|---|---|---|---|
| HXB2 | LeuIleHisSerLeuIleGluSerGlnAsnGlnGluLysAsnGluGlnGluLeu | | 660 |
| BRU | ———————————————————————————————————— | | 665 |
| MN | ————Tyr————Leu——Lys————Thr——————————— | | 661 |
| SC | ————————Tyr Thr————————————————————— | | 660 |
| SF2 | ————Thr——Tyr Thr——Leu——————————————— | | 659 |
| NY5 | | | |
| CDC4 | ————————Tyr Thr————————————Gln——————— | | 670 |
| WMJ2 | ————————Ile————Tyr————————————Gly——— | | 651 |
| RF | ————————Ile——Tyr Asn——Leu——————————— | | 669 |
| MAL | ————————Ile——Tyr Asn——————————Ile————Lys——— | | 662 |
| ELI | ————————————Tyr————————————Thr————Lys——— | | 657 |
| Z6 | ————————————Tyr Arg————————————Thr——— | | 659 |
| Z3 | | | |
| Z321 | Val————Tyr Asn————————————Thr————Ile————ArgAsp——— | | 660 |
| JY1 | Val————Tyr————————Asn————Ile————Asp——— | | 667 |

|       | TyrIleLysLeuPheIleMetIleValGlyGlyLeuValGlyLeuArgIleValPheAla |     |
|-------|---|-----|
| HXB2  |                                                              | 700 |
| BRU   | ———Ile———————————————————————————————————————————————————————— | 705 |
| MN    | ———Ile———————————————————————————————————————————————————————— | 701 |
| SC    | ———Ile——————————————————————————————————————————————————Thr—— | 700 |
| SF2   | ———Ile———————————————————————————————————————————————————————— | 699 |
| NY5   |                                                              |     |
| CDC4  | ———Ile————————————————————————————Ile———————————————————————— | 710 |
| WMJ2  | ———Ile————————————————————————————Ile———————————————————Thr—— | 691 |
| RF    | ———ArgIle—————————————————————————Ile——————————Lys——————————— | 709 |
| MAL   | ———ArgIle———IleVal————————————————Ile————————————Ile————————— | 702 |
| ELI   | ———Ile——————————————————Ile———————Ile———————————————————————— | 697 |
| Z6    | ———Ile————————————————————————————Ile———————————————————————— | 699 |
| Z3    |                                                              |     |
| Z321  | ———Ile————————————————————————————Ile———————————————————————— | 700 |
| JY1   | ———Ile————————————————————————————Ile——————————————————Thr——— | 707 |

FIG. 2-13C

| | | 3' sj |  |
|---|---|---|---|
| HXB2 | ValLeuSerIleValAsnArgValArgGlnGlyTyrSerProLeuSerPheGlnThrHis | | 720 |
| BRU | ---------------------------------------------------------- | | 725 |
| MN | -------------------------------------------Leu------Arg--- | | 721 |
| SC | ------------------------------------------------------Arg--- | | 720 |
| SF2 | ------------------------------------------------------Arg--- | | 719 |
| NY5 | | | |
| CDC4 | ----------------------------------------------------Leu--- | | 730 |
| WMJ2 | ---------------------------------------------------------- | | 711 |
| RF | ---------------------------------------------------------- | | 729 |
| MAL | ------Leu---------------------------------Leu-------------- | | 722 |
| ELI | ------Leu-------------------------------------------------- | | 717 |
| Z6 | ------Leu-------------------------------------------Leu--- | | 719 |
| Z3 | | | |
| Z321 | ---------------Ile-----------------------------------Leu--- | | 720 |
| JY1 | ------Leu--------------------------------------------Leu--- | | 727 |

FIG. 2-14A

|       | <- tat cds end |     |
|-------|----------------|-----|
| HXB2  | LeuProIleProArgGlyPro...AspArgProGluGlyIleGluGluGluGlyGlyGlu | 739 |
| BRU   | ---Thr--- | 744 |
| MN    | ---Pro---Val--- | 740 |
| SC    | ---SerGln--- | 739 |
| SF2   | ---Val---Asp--- | 738 |
| NY5   | | |
| CDC4  | ---Asn---Thr---Gly--- | 749 |
| WMJ2  | ---Thr--- | 730 |
| RF    | ---Ala---Gly--- | 748 |
| MAL   | ---Thr---Pro--- | 742 |
| ELI   | ---Ala---Thr--- | 736 |
| Z6    | ---Ala--- | 738 |
| Z3    | ---Glu--- | |
| Z321  | ThrHisHisGln---Glu---Arg---Gly--- | 739 |
| JY1   | ---Ala--- | 746 |

FIG. 2-14B

|       | ArgAspArgAspArgSerIleArgLeuValAsnGlySerLeuAlaAlaLeuIleTrpAspAsp |      |
|-------|------|------|
| HXB2  | [                                                          ] | 759  |
| BRU   | ---------------------------------------------------------- | 764  |
| MN    | ------Thr----Gly-----------His----Phe----Ile----Val------- | 760  |
| SC    | ----------------Gly-----------Asp----Phe----Ile----Val---- | 759  |
| SF2   | ----------------Val-----------Asp----Phe-----------Glu---- | 758  |
| NY5   | ---------------------------------------------------------- |      |
| CDC4  | ----Gly----Gly----Thr---------His----Phe-----------Val---- | 769  |
| WMJ2  | ------------Gly---Val---------His----Phe------------------ | 750  |
| RF    | ------------GlyGlyAla---------------Phe----Thr------------ | 768  |
| MAL   | ----GlnGly----Gly---------------------PheSer-------------- | 762  |
| ELI   | ----Gly-----------Val----Leu----------PheSer-------------- | 756  |
| Z6    | ----Gly-------------------------------PheSer-------------- | 758  |
| Z3    | ---------------------------------------------------------- |      |
| Z321  | Gln--------------------------Ser----Phe----Pro----Ala----- | 759  |
| JY1   | GlnGly-----------------------------PheSer---------Phe----- | 766  |

FIG. 2-14C

| | | | |
|---|---|---|---|
| HXB2 | *<br>LeuArgSerLeuCysLeuPheSerTyrHisArgLeuArgAspLeuLeuLeuIleValThr | | 779 |
| BRU | ------------------------------------------------------------ | ------ | 784 |
| MN | ---------------Phe------------------------------------------ | ---His.---AlaAla--- | 779 |
| SC | +++--------------------------------------------------------- | ------ | 779 |
| SF2 | ------------------------------------------------------------ | ------AlaAla--- | 778 |
| NY5 | ---------------------------------Arg----------------------- | | |
| CDC4 | ------------------------------------------------------------ | ---Ala--- | 789 |
| WMJ2 | ------------------------------------------------------------ | ---Lys--- | 770 |
| RF | ---TrpThr--------------------------------------------------- | ---Val--- | 788 |
| MAL | ---Asn------------------------------------------------------ | ---Ala--- | 782 |
| ELI | ------------------------------------------------------------ | Ile---AlaVal--- | 776 |
| Z6 | ---Asn------------------------------------------------------ | Ile---AlaAla--- | 778 |
| Z3 | | | |
| Z321 | ------Cys--------------------------------------------------- | CysAla---AlaAla--- | 779 |
| JY1 | ---Asn------------------------------------------------------ | Ile---Ala--- | 786 |

FIG. 2-15A

| | | |
|---|---|---|
| HXB2 | ArgIleValGluLeuLeuGlyArgArgGlyTrpGluAlaLeuLysTyrTrpTrpAsnLeu | 799 |
| BRU | ------------------------------------------------------------ | 804 |
| MN | -----------------------------Val---------------------------- | 799 |
| SC | ------------------------------------------------------------ | 799 |
| SF2 | ---Thr----Ile----His--------------------------------Ser----- | 798 |
| NY5 | | |
| CDC4 | ---------------------------------Val------------------------ | 809 |
| WMJ2 | ------------------------------------------------------------ | 790 |
| RF | ------------------------------------------------------------ | 808 |
| MAL | ---------------------------------------------Leu------------ | 802 |
| ELI | ------------------------------------------AspIle------------ | 796 |
| Z6 | ---------------------------------------------Leu------------ | 798 |
| Z3 | | |
| Z321 | ---Thr----Ile-------------------------------Thr----LeuGly--- | 799 |
| JY1 | ---------------Ile-------------------------------Leu----Ser- | 806 |

FIG. 2-15B

|        | <-- trs/art cds end [                                              ] |     |
|--------|---------------------------------------------------------------------|-----|
| HXB2   | LeuGlnTyrTrpSerGlnGluLeuLysAsnSerAlaValSerLeuAsnAlaThrAla           | 819 |
| BRU    | ------------------------------------------------------------------- | 824 |
| MN     | -------------------------------Ser--------------------------------- | 819 |
| SC     | ------------------------Arg---------------------------------------- | 819 |
| SF2    | -------------Ile--------------------PheVal------------------------- | 818 |
| NY5    | -------------------------------------Trp--------------------------- |     |
| CDC4   | ------------------------Val--Val----------------------------------- | 829 |
| WMJ2   | ----------Lys--------------------------Ile------------------------- | 819 |
| RF     | ------------------Gly---------------Thr---------------------------- | 828 |
| MAL    | ----------Gly-------------Ile-------Thr---------------------------- | 822 |
| ELI    | ----------Arg-------Ser--------PheAsp----Ile----------------------- | 816 |
| Z6     | ---Arg---Arg--------Ser--------------AspThrIle--------------------- | 818 |
| Z3     |                                                                     |     |
| Z321   | ValIle----Gly-----------IleAsn----AspThrVal------------------------ | 819 |
| JY1    | ----------Thr-------PheIle----------------------------------------- | 826 |

FIG. 2-15C

| | | | |
|---|---|---|---|
| HXB2 | IleAlaValAlaGluGlyThrAspArgValIleGluValValGlnGlyAlaCysArgAla * | | 839 |
| BRU  | ------------------------------------------------------------ | | 844 |
| MN   | ---------------------------------------Leu---Arg---Gly------ | | 839 |
| SC   | ---------------------------------------LeuLeu---Arg---Phe--- | | 839 |
| SF2  | ---------Thr-----------------------------Ala---Arg---Tyr---- | | 838 |
| NY5  | ------------------------------------------------------------ | | |
| CDC4 | --------------------------------------------ArgIleTyr------- | | 849 |
| WMJ2 | --------------------------------------------ArgIle---------- | | 830 |
| RF   | ----------------------------Ile-------Ala---ArgIleLeu------- | | 848 |
| MAL  | ------------------------Cys-------------IleGly---ArgPheGly-- | | 842 |
| ELI  | ---------------------------------------------IleIle---Arg--- | | 836 |
| Z6   | ------------------------------------------Ile---ArgArgThrTyr | | 838 |
| Z3   | ------------------------------------------------------------ | | |
| Z321 | ----------------AspTrp------------------------Arg---Gly----- | | 839 |
| JY1  | ------------------------------Ile------LeuIleArgArg---Phe--- | | 846 |

FIG. 2-16A

| Strain | Sequence | | | Position |
|---|---|---|---|---|
| HXB2 | IleArgHisIleProArgArgIleArgGlnGlyLeuGluArgIleLeuLeu+++ | | | 857 |
| BRU | ------------------------------------------------------ | | | 862 |
| MN | ---Leu------Thr-------------------------------Ala------ | | | 857 |
| SC | ---Leu------Thr-------------------------------Ala---Gln--- | | | 857 |
| SF2 | ---Leu------His-------------------------------Leu--- | | | 856 |
| NY5 | | | | |
| CDC4 | PheLeu-----------------------------Phe---Ala------ | | | 867 |
| WMJ2 | ---Ile-----------------------------------Ala------ | | | 848 |
| RF | PheLeu-----------------------------------Ala------ | | | 866 |
| MAL | ---Leu-----------------------------Phe---Ala------ | | | 860 |
| ELI | ValLeuAsn--------------------------------Ser------ | | | 854 |
| Z6 | ValLeuAsnVal---Thr-----------------------Leu------ | | | 856 |
| Z3 | | | | |
| Z321 | PheLeuAsn-------------------------------Ala------ | | | 857 |
| JY1 | ValLeu-----------Val---------------------Ala------ | | | 864 |

FIG. 2-16B

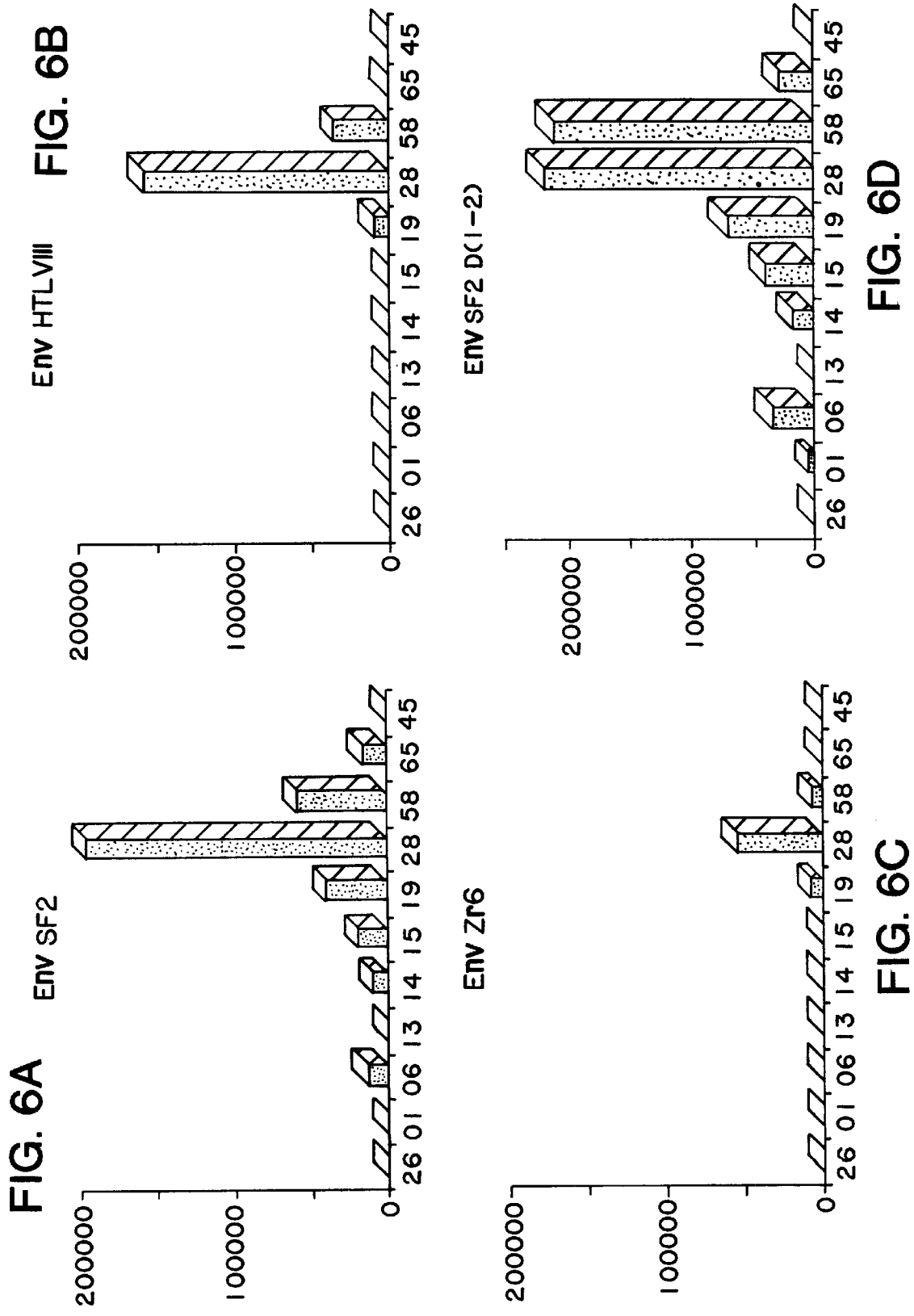

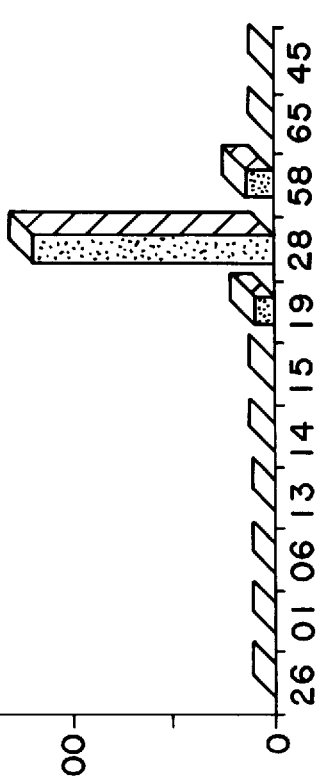
FIG. 6E  Env SF2 D3E
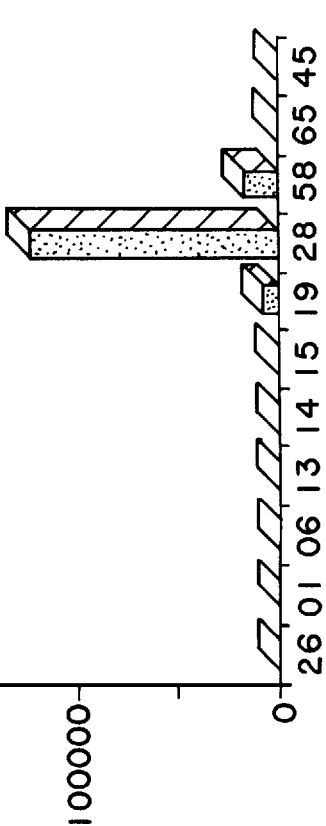
FIG. 6F  EnvSF2 D(3-5)
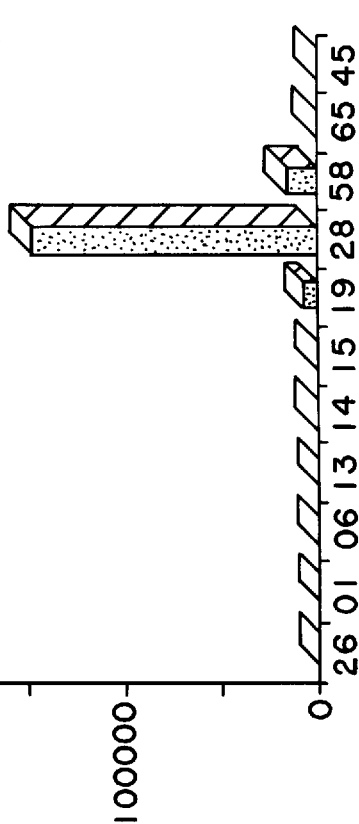
FIG. 6G  Env SF2 D(1-5)

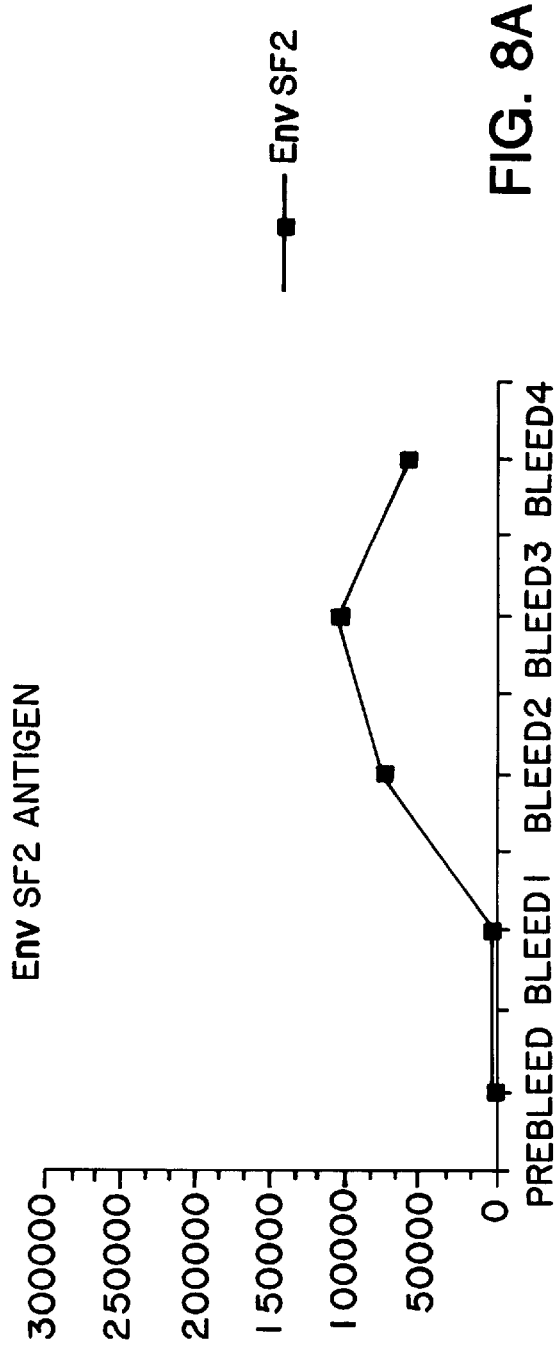
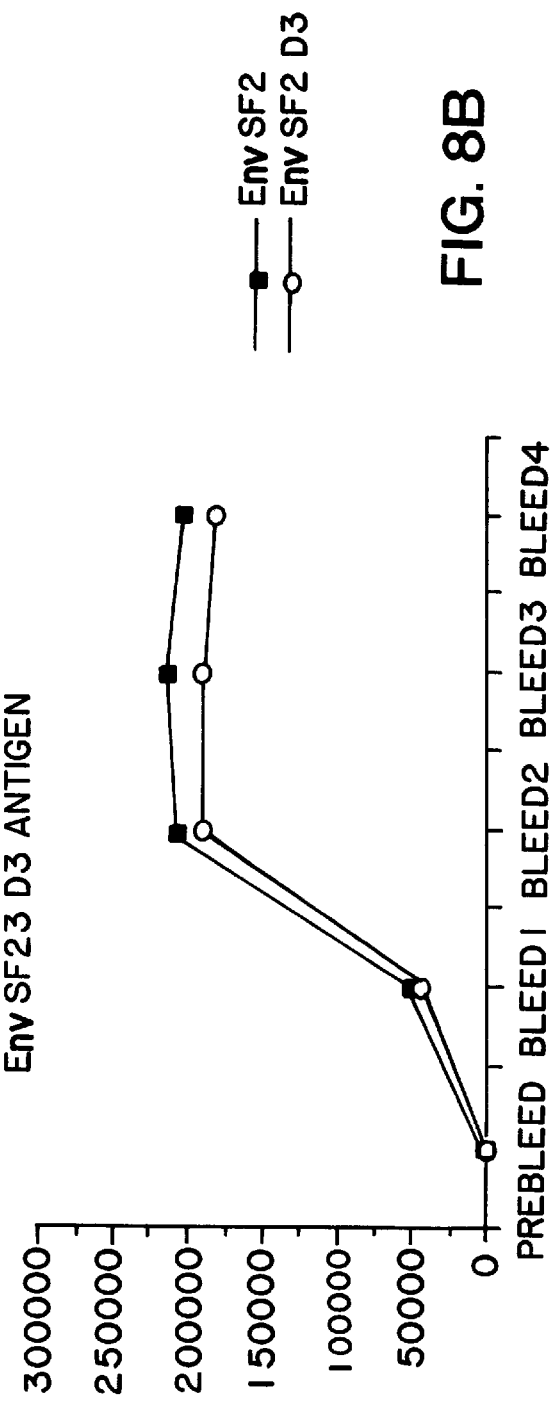
FIG. 8A
FIG. 8B

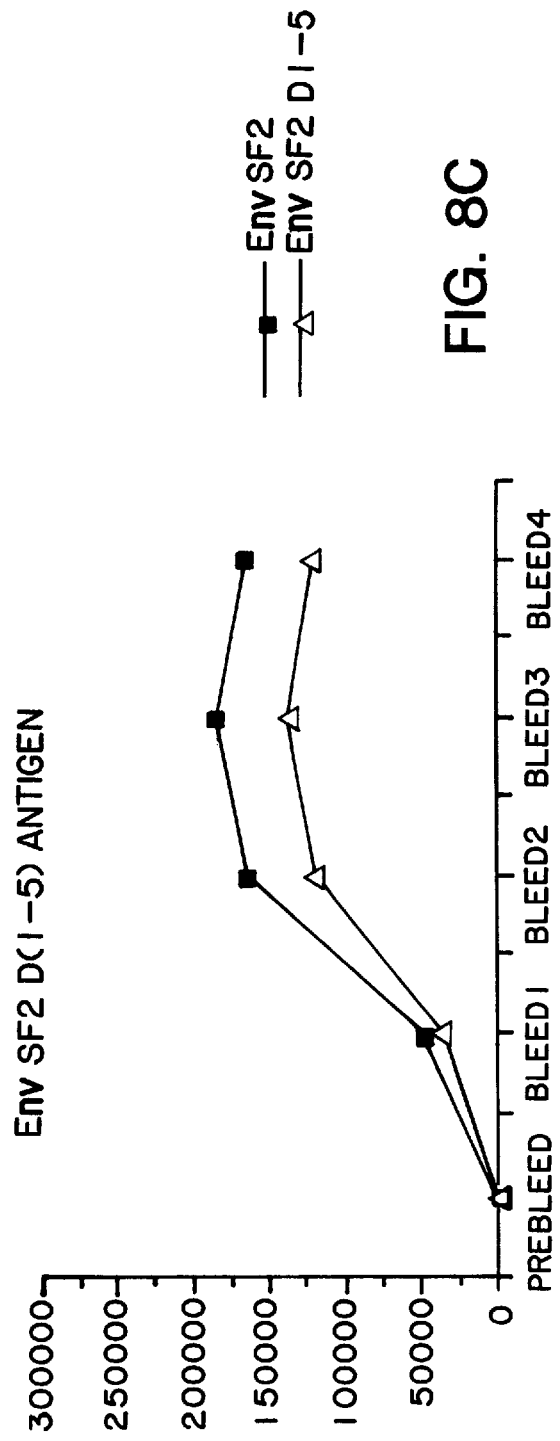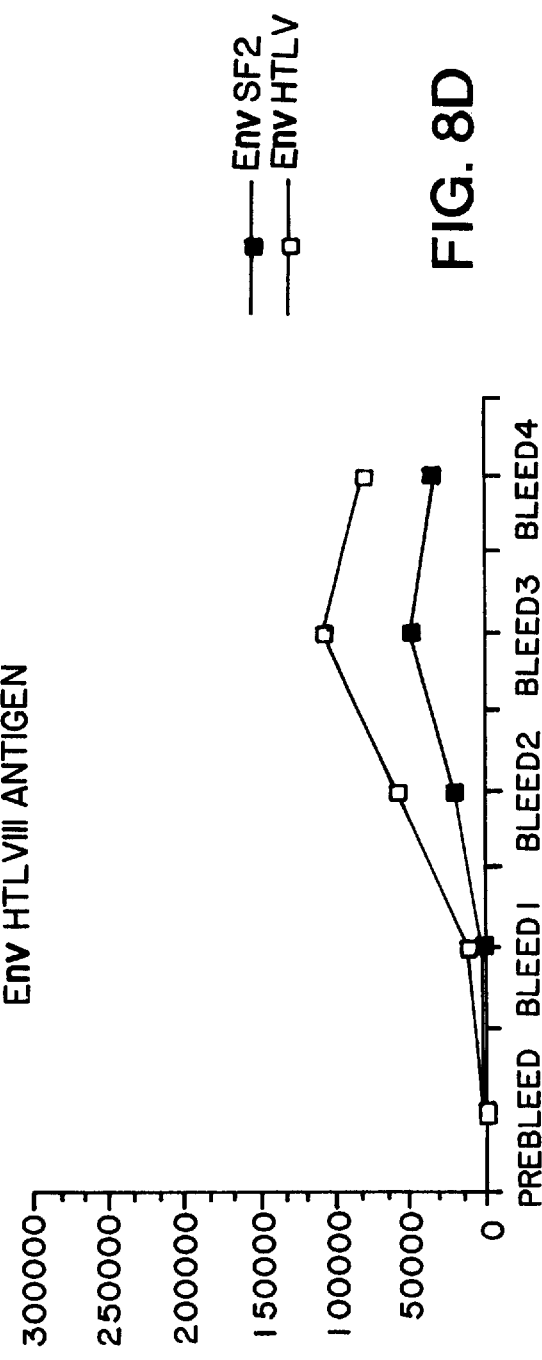

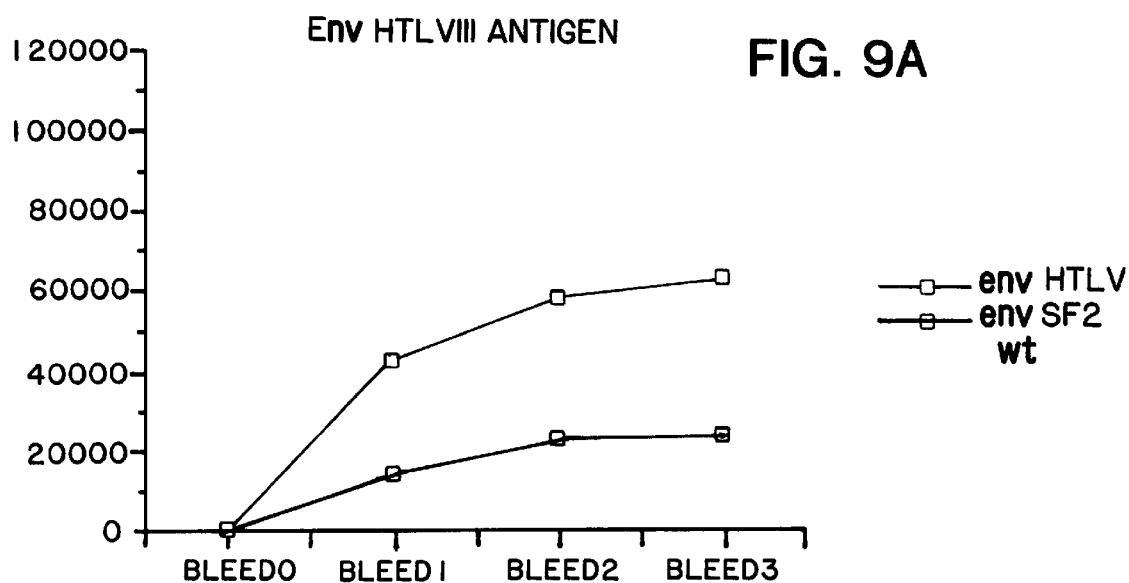
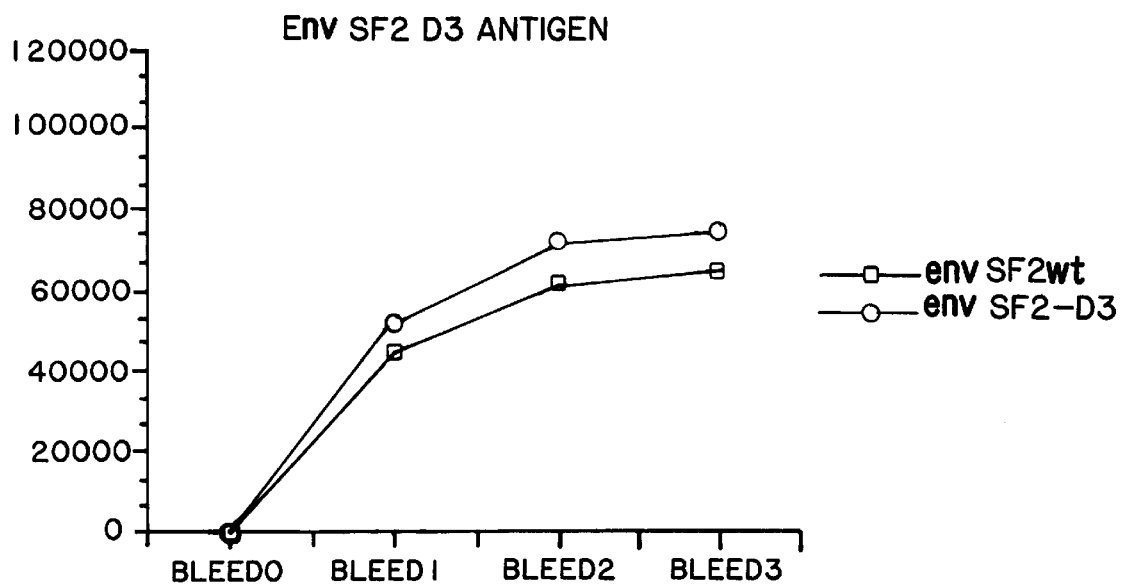

DNA SEQUENCES ENCODING HIV-1 ENVELOPE MUTEINS CONTAINING HYPERVARIABLE DOMAIN DELETIONS

This application is a divisional of application Ser. No. 08/371,618, filed Jan. 12, 1995, which is a continuation of application Ser. No. 08/006,252 filed Jan. 19, 1993, now abandoned, which is a continuation of application Ser. No. 07/243,944 filed Sep. 13, 1988, now abandoned.

TECHNICAL FIELD

The present invention is directed to novel analogs (muteins) of the envelope proteins from human immunodeficiency virus type 1 (HIV-1), methods of making the analogs, DNA sequences encoding the analogs, and methods of using the analogs, for example, in immunoassays and vaccine compositions.

BACKGROUND

HIV-1, and a recently identified related virus named HIV-2, are the known causative agents of Acquired Immune Deficiency Syndrome (AIDS). Many isolates of HIV-1 have been identified and sequenced. A striking feature of these independent isolates is substantial genomic and amino acid variation, centered particularly in the envelope gene and proteins. This variation among HIV-1 isolates has important implications for both AIDS diagnostics and potential vaccines.

Starcich et al., (1986) *Cell* 45:637–648, reports on the genetic variation in five independent HIV-1 isolates, as well as variations in deduced amino acid sequences. Both conserved and variable regions were observed.

Coffin, (1986) *Cell* 46:1–4, is a review directed to the variation in the envelope of HIV-1, and the possible mechanism which brings about the variation. Coffin hypothesized that the highly variable domains, termed "hypervariable" domains, are masking epitopes within the conserved domains from being available for neutralizing antibodies or cell-mediated immune responses. It is concluded that vaccination strategy for HIV-1 should be directed towards developing the ability to provoke an immune response directed against the conserved regions of the envelope despite the presence of masking variable domains.

Modrow et al., (1987) *J. Virol.* 61:570–578, is also directed to comparison of the amino acid sequences of various HIV-1 isolates. Computer analysis was employed to predict epitopes in the envelope protein, and it was found that the majority of predicted epitopes were located in the hypervariable regions. See, e.g., FIG. 1 and Tables 1 & 2, incorporated herein by reference.

Hahn et al., (1986) *Science* 232:1548–1553, discloses the sequence variations in a series of HIV-1 isolates from a single individual, particularly in the envelope. See also Saag et al., (1988) *Nature* 334:440–444; Fisher et al., (1988) *Nature* 334:444–447.

Rusche et al., (1988) *Proc. Natl. Acad. Sci. USA* 85:3198–3202, discloses that a short peptide having the sequence of an HIV-1 isolate in the third hypervariable domain of the envelope protein was able to absorb isolate-specific neutralizing antibodies from antisera, and that another group was able to elicit isolate-specific neutralizing antibodies by immunization with a peptide from the same domain. It is suggested that since this neutralizing epitope is found in one of the hypervariable domains., that a possible vaccination strategy is to prepare a subunit antigen made up of the critical epitope from multiple isolates. See also Looney et al. (1988) *Science* 241:357–359.

Goudsmit et al., (1988) *Proc. Natl. Acad. Sci. USA* 85:4478–4482, reports on the neutralizing ability of antibodies raised in chimpanzees infected with various HIV-1 isolates, and a rabbit immunized with an envelope subunit. The epitope identified by Rusche et al. is reported to be an isolate-specific neutralizing epitope, and that it is immunodominant in HIV-1 chimpanzees.

Due in large part to the generally accepted view that attenuated or killed virus vaccines for AIDS are not feasible, the primary focus for the development of vaccines has been the subunit antigens. Several groups have suggested that short oligopeptides from the envelope domain would make suitable subunit antigens. Other groups are pursuing live recombinant virus vaccines, natural or recombinant viral polypeptide vaccines, or anti-idiotype vaccines. See, e.g., Koff et al., (1988) Science 241:426–432 (and references cited therein).

A continuing need exists to develop new and better HIV-1 envelope analogs, as well as polypeptides that avoid isolate-specific immune interactions for use in diagnostics and as potential vaccines.

SUMMARY OF THE INVENTION

The present invention is directed to HIV-1 envelope analogs (muteins) comprising the constant domains of gp120env or gp160env, but lacking at least one epitope from a hypervariable domain. Despite the reports in the literature suggesting the importance of the epitopes in the hypervariable domains (e.g., immunodominant and/or neutralizing), it has surprisingly been discovered that the muteins of the present invention are useful as diagnostic reagents exhibiting at least as great or greater reactivity to antibodies raised against diverse isolates, and as antigens in raising nonisolate-specific antibodies upon immunization of a mammal.

In one embodiment, the present invention comprises an improved analog of HIV-1 gp120env or gp160env wherein the improvement comprises the deletion of at least one epitope within a hypervariable domain, while retaining the domains conserved among HIV-1 isolates.

In another embodiment, the present invention is directed to a polypeptide comprising epitopes bound by antibodies to HIV-1 gp120env or gp160env and an amino acid sequence according to the formula:

C1-V1-V2-C2-V3-C3-V4-C4-V5-C5 wherein:

C1 is an amino acid sequence substantially homologous to Ser29 through Cys130 of HIV-1 SF2;

C2 is an amino acid sequence substantially homologous to Cys199 through Leu291 of HIV-1 SF2;

C3 is an amino acid sequence substantially homologous to Ser366 through Cys387 of HIV-1 SF2;

C4 is an amino acid sequence substantially homologous to Cys415 through Gly456 of HIV-1 SF2;

C5 comprises an amino acid sequence substantially homologous to Phe466 through Arg509 or Leu855 of HIV-1 SF2;

V1 is an amino acid sequence of 0 to a maximum of about 30 residues;

V2 is an amino acid sequence of 0 to a maximum of about 50 residues;

V3 is an amino acid sequence of 0 to a maximum of about 90 residues;

V4 is an amino acid sequence of 0 to a maximum of about 30 residues; and

V5 is an amino acid sequence of 0 to a maximum of about 10 residues;

with the proviso that at least one of the V domains selected from the group consisting of V1, V2, V3, V4 and V5 contains no more than about one-third of the said maximum number of residues for the V domain.

Still another embodiment of the present invention is directed to a polypeptide analog of HIV-1 gp120env or gp160env comprising (a) about 300 to about 850 amino acid residues in length; (b) constant domains, in the N-terminal to the C-terminal direction, Ser29-Cys130 of HIV-1 SF2 (C1), Cys199-Leu291 of HIV-1 SF2 (C2), Ser366-Cys387 (C3), Cys415-Gly456 (C4) of HIV-1 SF2, and Phe466-Arg509 or Phe466-Leu855 of HIV-1 SF2 (C5), or domains substantially homologous to said C1, C2, C3, C4 or C5; and (c) the intervening domains, if any, located between said constant domains comprising sequences found between substantially homologous constant domains in native HIV-1 gp120env, with the proviso that at least one of said intervening domains between said constant domains is either missing or missing an epitope.

The present invention is also directed to an immunoassay for the detection of antibodies to HIV-1 comprising: (a) providing a liquid sample to be tested for the presence of anti-HIV-1 antibodies; (b) contacting said sample with a polypeptide as described above under conditions whereby any anti-HIV-1 antibodies present in said sample may bind to an epitope to provide sample-contacted polypeptide; and (c) detecting any antibody bound to said sample-contacted polypeptide.

In yet another embodiment, the present invention is directed to a method of selectively raising antibodies in a mammal to epitopes in the constant domains of human immunodeficiency virus type 1 (HIV-1) gp120env or gp160env comprising administering to said mammal a polypeptide as described above, whereby antibodies to said polypeptide are produced in response to said administration.

The present invention is also directed to a composition useful in such method comprising the polypeptide described above in combination with a pharmaceutically acceptable carrier.

The present invention is also directed in another embodiment to a DNA sequence encoding the above polypeptide, as well as a cellular host comprising the DNA sequence under the control of transcriptional and translational control sequences whereby the polypeptide encoded by the DNA sequence is expressed by the cellular host. The present invention is also directed to methods of producing the above polypeptide by growing a culture of the above cellular host under conditions whereby the polypeptide encoded by the above DNA sequence is expressed, and recovering the polypeptide from the culture.

These and other embodiments of the present invention will be apparent to those of ordinary skill in the art.

DETAILED DESCRIPTION

HIV-1 is a known virus, of which many isolates have been observed. See, e.g., Levy et al., (1984) *Science* 225:840; Barre-Sinoussi et al., (1983) *Science* 220:868; Popovic et al., (1984) *Science* 224:497; *AIDS: Papers from Science,* 1982–1985 (R. Kulstad ed. 1986); *Current Topics in AIDS* (M. Gottlieb et al. eds. 1987). The envelope gene of HIV-1 produces a precursor glycoprotein of approximately 160 mw, referred to as gp160. or gp160env. The precursor is cleaved during expression to provided gp120 (gp120env), the major exterior envelope glycoprotein, and gp41 (gp41env), the transmembrane protein. Various HIV-1 isolates have been reported in the literature, including, BH10, PV22, BRU, HXB2, WMJ1, WMJ2, WMJ3, CDC4, HTLV-IIIRF, HTLV-IIIB, Z3, Z6, Z321, MAL, NY5, ELI, JY1, LAV1A, and HAT3. Of particular interest to the present invention is HIV-1 isolate SF2, originally designated ARV2. See, e.g., Levy, U.S. Pat. No. 4,716,102; Levy et al., (1984) Science 225:84; EPO Pub. No. 181,150.

Figure 1:
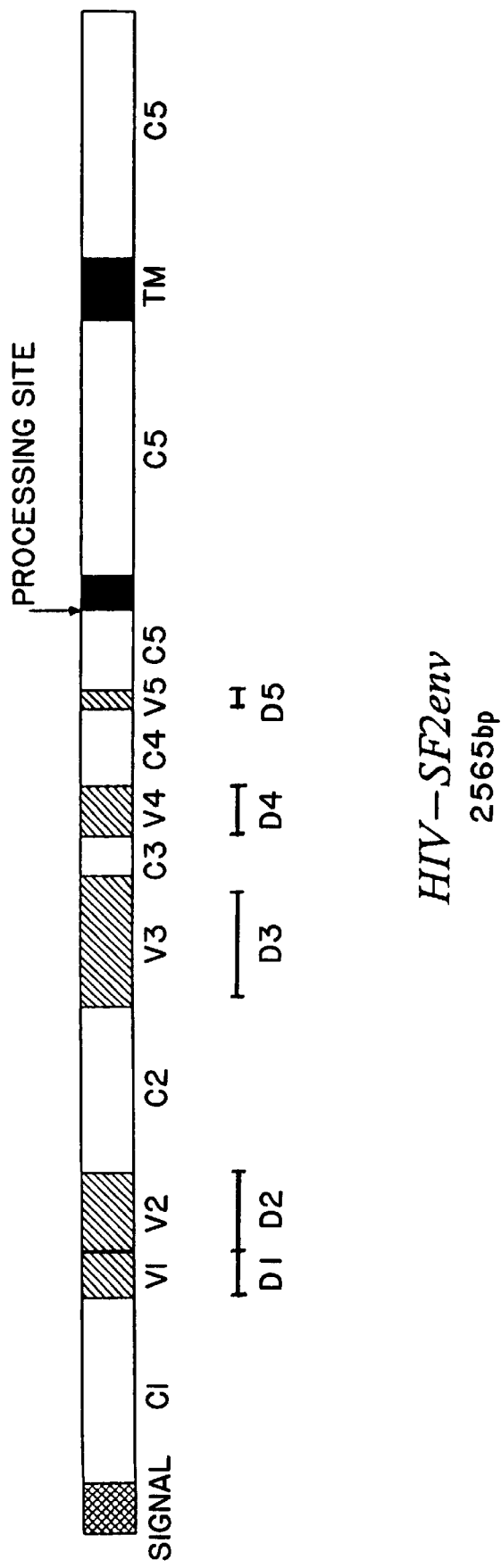
FIG. 1 is a schematic diagram of the wild-type gp120env gene from HIV-SF2.

The conserved and hypervariable domains of HIV-1 envelope proteins have been described previously. See, e.g., Modrow et al., supra. FIG. 1 herein is a schematic diagram showing the location of the five hypervariable regions (V1, V2, V3, V4 and V5) and the five constant regions (C1, C2, C3, C4 and C5) in the envelope gene from HIV-1 SF2. Various deletions encompassing part or all of a hypervariable domain are also shown (D1, D2, D3, D4 and D5). Two regions of predominantly hydrophobic amino acids are denoted by dark shading, where the transmembrane anchor has been labeled TM. The signal sequence is highlighted at the N-terminus, as well as the processing site separating gp120env (positions 1–1527) from gp41env (positions 1528–2565).

Hypervariable domains are characterized by a substantial lack of homology (e.g., as low as 10%) among independent HIV-1 isolates. Furthermore, there is a substantial variation in length among the hypervariable domains from various isolates due to the prevalence of insertion and deletion mutations. Thus, these regions cannot be characterized from one isolate to the next by having any substantial degree of amino acid sequence homology, and can only be assigned an approximate length. The primary characterization of hypervariable domains is their location within the envelope glycoprotein and their presumed tertiary structure (i.e., loops).

The conserved or constant domains, as well as all 18 cysteines in the envelope, are highly conserved. Corresponding hypervariable domains are found to be located identically relative to surrounding constant domains and cysteines from one isolate to the next. Furthermore, the tertiary structure of the hypervariable domain appears to be highly conserved; e.g., two nonhomologous hypervariable domains from different HIV-1 isolates will usually both exhibit the same three-dimensional conformation, such as an exposed loop. Thus, hypervariable domains from new HIV-1 isolates can be readily identified by sequencing the new isolates and comparing the sequence to known HIV-1 sequences so that the conserved domains and cysteines are aligned. See, e.g., Modrow et al., supra and FIG. 2 herein.

Figures 2, 3, 4, 5, 5A:
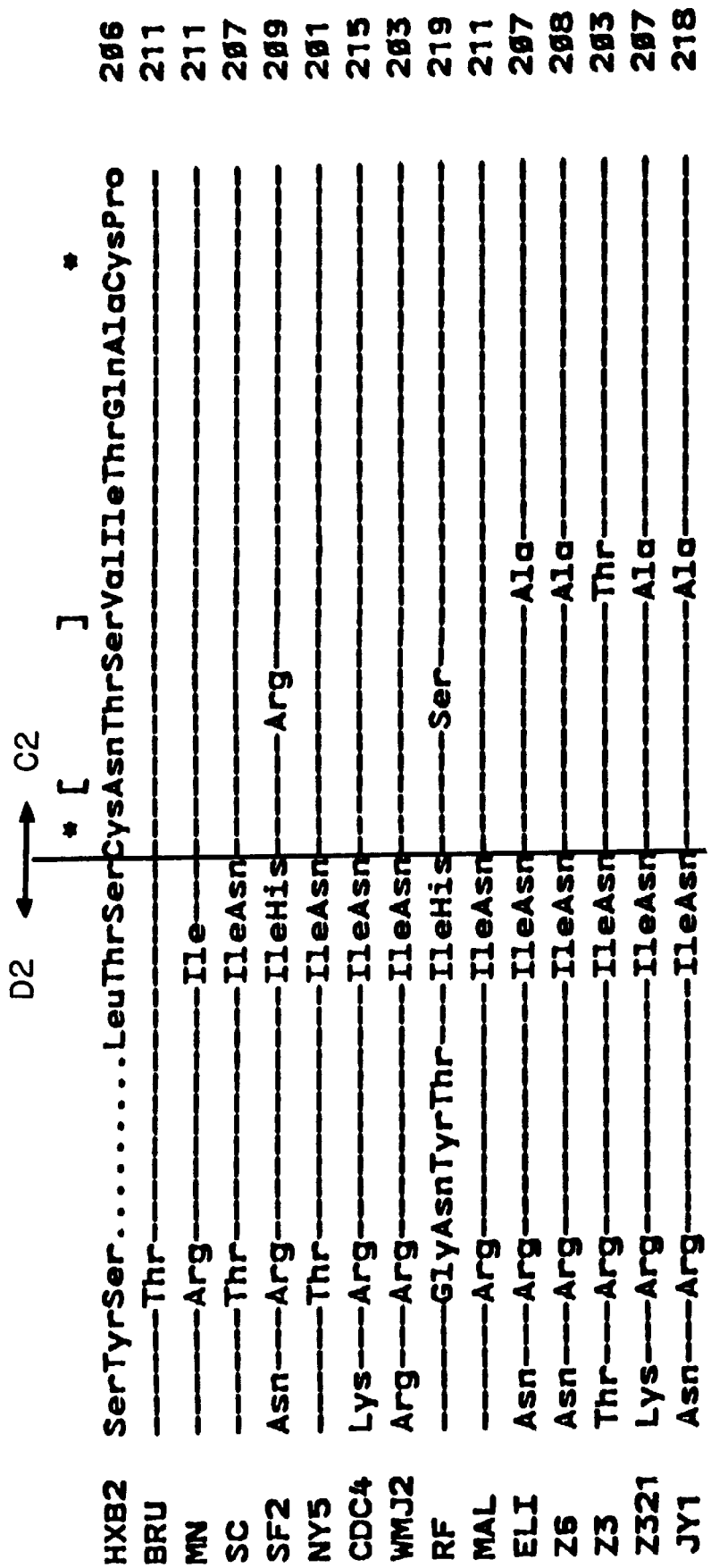
FIG. 2 shows the alignment of amino acid sequences for various HIV-1 isolates, including SF2, with the constant and variable domains indicated. Potential N-linked glycosylation sites, for the HXB2 sequence only, are indicated by "[ ]"; cysteine residues have "*" above them.
FIG. 3 is a restriction map of mammalian expression vector pSV7dARV120tpa.
FIG. 4 is a restriction map of mammalian expression vector pCMV6ARV120tpa.
FIG. 5 is a restriction map of yeast expression vector pHL15.

The location of the various domains, both constant and hypervariable, will be described hereinafter with reference to the sequence and numbering of the HIV-1 SF2 isolate. It is to be understood that this is for convenience only; the invention is not limited to analogs containing only HIV-1 SF2 sequences, but also encompasses analogs employing corresponding domains or sequences from other isolates. A domain from another HIV-1 isolate envelope protein can be easily identified as corresponding to an SF2 sequence by those of ordinary skill in the art by alignment of the conserved domains and the 18 cysteines of both isolates. Such an alignment is shown in FIG. 2, where the corresponding sequences of 15 HIV-1 isolates are aligned. The cysteine residues are marked with an asterisk, and potential N-linked glycosylation sites for the HXB2 isolate are indicated by "[ ]". The cleavage site for the signal peptide and for the mature gp120env and gp41env proteins are shown, along with the constant domains, C1-C5. Specific deletions, D1-D5, are also shown in the figure.

The constant domains of the SF2 isolate are as follows: C1, Ser29-Cys130; C2, Cys199-Leu291; C3, Ser366-Cys387; C4, Cys415-Gly456; and C5, which is Phe466-Arg509 for gp120env analogs, or Phe466-Leu855 for gp160env analogs. Since these domains are highly conserved among HIV-1 isolates, the corresponding sequences from isolates other than SF2 will be substantially homologous to these SF2 domains; i.e., a minimum of about 70–75% amino acid sequence homology, with certain highly conserved domains exhibiting a minimum of about 80%, or even 85–90% homology. The differences in amino acid sequences found in these conserved domains are generally attributable to point mutations in the nucleic acid sequence, as opposed to the deletion and insertion mutations which typify the differences in hypervariable domains.

As shown in FIGS. 1 and 2, the hypervariable domains lie between the conserved domains, C1-C5. Not all of the amino acids in these intervening domains, however, comprise hypervariable regions. Indeed, due to the heterogeneity among HIV isolates in the hypervariable domain, it is not feasible to generally define precise limits of the hypervariable domain. Thus, for the convenience of describing the present invention, the domains between the constant domains will be referred to as "variable" or "intervening" domains, and it will be understood that they may comprise both hypervariable regions as well as less variable, yet not highly conserved, sequences. Thus, the analogs of the present invention can be described schematically according to the following formula:

$$C1-V1-V2-C2-V3-C3-V4-C4-V5-C5 \quad (I)$$

C1-C5 and V1-V5 in formula I are defined as described above in the Summary of the Invention. V1-V5 consist of the variable or intervening domains which contain hypervariable regions. The polypeptides of the present invention will contain a deletion in at least one of these variable domains when compared to a native gp120env or gp160env. The deletions will typically be at least about one-third of the variable domain, and oftentimes will consist of a deletion of the entire variable domain. Furthermore, it is also preferred to delete sequences from more than one of the variable domains, including the deletion of all five of the variable domains in their entirety. Thus, in accordance with the present invention, any of the variable domains, V1-V5, can be anywhere from zero to a maximum number of amino acids in length, the maximum being an approximation of the longest of such domains found in HIV-1 isolates. At least one of the V domains, however, will have deleted therefrom at least one-third of that maximum number of amino acids, or one-third of the length of the corresponding domain from the homologous HIV-1 isolate.

Since the variable or intervening domains of formula I can comprise more than the true hypervariable domains, a selected Vn domain can be expressed by the following formula:

$$Sn—HVn—Sn' \quad (II)$$

wherein n is 1, 2, 3, 4 or 5 (as in V1, V2, etc.), HVn is a hypervariable domain of x amino acid residues in length, and Sn and Sn' are nonhypervariable sequences flanking HV in the Vn domain, the flanking sequences being y and y' residues in length, respectively. In the native protein, the sum of x, y and y' equals the maximum number of residues for Vn in a chosen isolate, and y and/or y' may be zero. As for the analogs of the present invention, the sum of x, y and y' will be anywhere from zero to the maximum number. The actual values for x, y and y' for a particular Vn can be determined by sequence comparison of a representative number of HIV-1 isolates. See, e.g., FIG. 2 and Modrow et al., supra.

The following are the intervening domains of the SF2 isolate, which can be used for comparison purposes to determine the corresponding intervening domains in other HIV-1 isolates. See, e.g., FIG. 2. V1 of SF2 is about 24 amino acids in length, encompassing Thr131 through Asn154 and, optionally, Cys155. This C-terminal cysteine is one of the 18 highly conserved cysteine residues found in gp120env. The corresponding domains from independent HIV-1 isolates sequenced to date appears to range from about 22 to about 31 amino acid residues in length. V2 of SF2 spans from Ser156 through Ser198. The corresponding domain in other HIV-1 isolates sequenced to date appears to range from about 39 to about 52 amino acid residues in length. V3 of SF2 spans Asn292 through Glu365, and the corresponding domains in other HIV-1 isolates sequenced to date appears to range from about 88 to about 90 amino acid residues in length. V4 of SF2 spans from Asn388 through Pro414, and the corresponding domains from other HIV-1 isolates appear to range from about 28 to about 33 residues in length. V5 of SF2 spans from Thr457 through Thr463, and corresponding domains from other HIV-1 isolates appear to range from about 10 to about 11 residues in length.

In selecting the areas of the intervening domains for deletions, it is preferred to either select those portions showing hypervariability, or areas known to encode epitopes which elicit a significant immune response in vivo. Examples of such epitopes in variable regions of the SF2 isolate include, without limitation, residues 137–158 (V1), residues 189–209 (V2), residues 300–327 (V3), residues 367–384 (V3), and residues 404–420 (V4). Corresponding epitopes from other isolates are known. Modrow et al., supra. Examples of preferred deletions for SF2, D1-D5, are shown in FIGS. 1 and 2: Thr131-Asn154 (D1), Ser156-His198 (D2), Thr300-His332 (D3), Asn388-Pro414 (D4), and Thr457-Thr463 (D5). The polypeptides of the present invention may also have deletions from more than one variable domain, for example, V1 and V2; V1, V2 and V3; V1, V2 and V5; V3, V4 and V5; or V1, V2, V3, V4, and V5.

In a preferred embodiment, the HIV-1 envelope analogs of the present invention have deleted therefrom an epitope found in the intervening domains which is bound by antibodies produced by a mammal infected or immunized with the particular HIV-1 isolate, or its native envelope protein. It is particularly preferred that the deleted epitopes are those which produce isolate-specific immunodominant responses in a mammal. While applicants do not wish to be bound by this theory, it is believed that the deletion of these variable epitopes unmasks epitopes in the conserved domains which then become visible to the immune system by virtue of the absence of the epitopes from the variable domains.

In general, the amino acid sequence according to formula I will range from about 300 to about 850 amino acid residues in length, the actual length not being critical. The sequence of formula I can be contained within a larger polypeptide, for example a fusion protein. Such fusion proteins can include, for example, a fusion between the N-terminal sequence of superoxide dismutase (human or yeast) or beta-galactosidase, where these non-HIV-1 sequences are fused to the N-terminal of the C1 domain. Alternatively, non-HIV-1 sequences could also be fused to the C-terminal of the C5 domain. The C1 domain may also be fused to a signal peptide (e.g., yeast alpha factor, or tpa signal) to provide for secretion of the HIV-1 envelope analog from a cellular host expressing the analog.

The HIV-1 envelope muteins of the present invention can be produced by any suitable method, such as direct peptide synthesis or recombinant DNA expression. The preferred method is to prepare the polypeptides by recombinant DNA techniques.

The methodology for preparing such recombinant polypeptides is within the skill of the art, and the techniques are fully explained in the literature. See, e.g., Maniatis et al., *Molecular Cloning: A Laboratory Manual* (1982); *DNA Cloning: A Practical Approach, Volumes I & III* (D. N. Glover, ed., 1985); *Oligonucleotide Synthesis: A Practical Approach* (M. J. Gate, ed., 1984); Perbal, *A Practical Guide to Molecular Cloning* (1984). The production of recombinant HIV-1 polypeptides is known in the art. See, e.g., Luciw et al., (1984) *Nature* 312:760; Sanchez-Pescador et al., (1985) *Science* 227:484; Hahn et al., (1984) *Nature* 312:167; Alizon et al., (1984) *Nature* 312:757; Ratner et al., (1985) *Nature* 313:636; Muesing et al., (1985) *Nature* 313:450; Wain-Hobson et al., (1985) *Cell* 40:9; EPO Pub. Nos. 181,150; 187,041; 227,169; 230,222; and PCT Pub. Nos. WO87/02038; WO87/02989; WO87/04459; WO87/04728. Methods of recombinant expression are also disclosed in commonly owned U.S. patent application Ser. No. 138,894, filed 24 Dec. 1987, entitled "Human Immunodeficiency Virus (HIV) Nucleotide Sequences, Recombinant Polypeptides, and Applications Thereof," the disclosure of which is incorporated herein by reference.

To prepare the polypeptides of the present invention by recombinant methods, a DNA coding sequence for the polypeptides must be provided. Such a coding sequence is a DNA sequence that can be transcribed and translated into a polypeptide in vivo when placed under the control of appropriate regulatory sequences. The boundaries of the coding sequence are determined by and include the translation start codon at the 5' (amino) terminus and a translation stop codon at the 3' (carboxy) terminus. DNA sequences encoding the polypeptides of the present invention can be prepared either by constructing a synthetic gene from overlapping oligonucleotides, or by site-directed mutagenesis of a sequence encoding native HIV-1 envelope. See, e.g., Zoller, & Smith (1983) *Meth. Enzymol.* 100:468–500.

DNA coding sequences for the polypeptides of the present invention can be maintained on a replicon, which is any genetic element (e.g., plasmid, cosmid, chromosome, virus) that functions as an autonomous unit of DNA replication in vivo; i.e., capable of replication under its own control. Vectors are replicons such as a plasmid, phage, or cosmid to which a DNA coding sequence may be attached so as to bring about the replication of the attached segment in vivo.

A host cell is then transformed with a DNA construct containing the coding sequence under the control of appropriate regulatory sequences in order to bring about the expression of the DNA coding sequence into the desired polypeptide. Cellular hosts can include, but are not limited to, bacteria (e.g., *E. coli, Bacillus subtilis, B. amyloliquefaciens, Salmonella typhimurium, Klebsiella pneumoniae* or *Erwinia amylouora*), yeast (e.g., *Saccharomyces cerevisiae, S. carlsbergensis, S. kluyveri, Kluyveromyces lactis,* Pichia, or Schizosaccharomyces), mammalian cells (e.g., CHO cells, COS cells, 293 cells or Xenopus oocytes), and insect cells (e.g., Drosophila embryos or *Spodoptera frugiperda*). The transformed cellular hosts may contain the DNA constructs encoding the polypeptides of the present invention either on an extrachromosomal element, or integrated into the chromosome.

Typically, the DNA coding sequence is placed into an expression cassette which comprises the DNA coding sequence flanked by appropriate regulatory sequences that control transcription initiation and termination within the cellular host. Preferably, the expression cassette contains convenient restriction sites at either end to permit convenient cloning of the cassette into an appropriate vector for transformation of the cellular host.

Transcription initiation and termination sequences recognized by the cellular host are DNA regulatory regions which flank a coding sequence are responsible for the transcription of an mRNA homologous to the coding sequence which can be translated into the desired polypeptide. Transcription initiation sequences include host promoter sequences, which are DNA regulatory sequences capable of binding RNA polymerase in a cell and initiating transcription of a downstream (3' direction) coding sequence. A coding sequence is "under the control" of transcription initiation and termination sequences when RNA polymerase binds the transcription initiation sequences and transcribes the coding sequence into mRNA terminating at the transcription termination sequence, and the mRNA is then translated into the polypeptide encoded by the coding sequence (i.e., expression).

Cellular hosts transformed with appropriate DNA constructs for the expression of polypeptides of the present invention are typically grown in a clonal population under appropriate conditions which bring about the expression of the DNA coding sequence of interest. The appropriate growth conditions will depend upon the cellular host and the transcriptional and translational regulatory sequences employed. Upon expression, the recombinant polypeptide is recovered from the culture by any appropriate method, e.g., gel chromatography, immunoabsorption, or gel electrophoresis.

Polypeptides of the present invention can be used as reagents in immunoassays for detecting the presence in a sample of either anti-HIV-1 antibodies or viral antigen. In an immunoassay for viral antigen, for example, polypeptides according to the present invention can be labeled and used as a competing antigen in a standard competitive ELISA or radioimmunoassay (RIA).

Configurations for immunoassays for antibodies to HIV-1 envelope vary widely, and the present invention contemplates the use of the polypeptides described herein in any such format. Such formats are well known in the art. See, e.g., *Immunoassay: A Practical Guide* (P. W. Chan & M. T. Perlstein, eds., 1987); McDougal et al., (1985) *J. Immunol. Meth.* 76:171–183; U.S. Pat. Nos. 4,629,783; 4,281,061; 4,520,113; 4,591,552; 4,134,792 (incorporated by reference herein). Whether the assay format is homogeneous or heterogeneous, and the measurement method is direct or indirect (e.g., competition), all such immunoassays have three common steps. First, a liquid sample suspected of containing the antibodies is provided. This sample is then contacted with polypeptides according to the present invention under conditions which will allow any antibodies having an epitope on the polypeptides to become bound thereto. Finally, there is a detecting step wherein it is determined whether or not any antibody bound to the polypeptide.

A preferred format for an anti-HIV-1 antibody assay is a heterogeneous immunoassay in which the polypeptides of the present invention are immobilized on, for example, a solid support. The selection of the appropriate solid support for immobilization of the polypeptide is conventional and within the skill of the art. In a typical assay, the sample suspected of containing the antibodies is contacted with the immobilized polypeptide and allowed to incubate under the appropriate conditions. The immobilized polypeptide is then separated from the sample and washed to remove any unbound antibody. The detecting step can constitute, for example, contacting the washed, immobilized polypeptide with an antibody that will recognize an epitope located on the anti-HIV-1 antibodies (i.e., anti-xenogenic), this second antibody being appropriately labeled for detection (e.g., radiolabeled, enzyme conjugated, avidin/biotin). After an appropriate incubation and washing step, the immobilized polypeptide is then assayed for the presence of the labeled second antibody. Alternatively, a competition immunoassay can be used where a labeled reference antibody to the immobilized polypeptide is incubated along with the sample suspected of containing the anti-HIV-1 antibodies, and the presence of such antibodies are determined by measuring a reduction or inhibition of binding of the labeled reference antibody to the immobilized polypeptide. See, e.g., PCT Pub. No. WO87/07957.

Kits suitable for immunodiagnosis and containing the appropriate labeled reagents are constructed by packaging the appropriate materials, including the polypeptides of the present invention and any antibodies used in the assay, in suitable containers along with remaining reagents and materials required by the assay format; e.g., incubation media, wash media, and means for measuring the presence of the analyte (e.g., enzyme-labeled antibodies and enzyme substrate). Other labels useful in the practice of immunoassays according to the present invention include radioisotopes and fluorescing compounds.

Polypeptides according to the present invention can be employed to selectively raise antibodies in a mammal to epitopes found in the constant domains of gp120env or gp160env. For example, parenterally administering polypeptides of the present invention to a mammal will cause an immune reaction in the animal, thereby producing antibodies to epitopes found in the conserved domains. Such antibodies can be recovered to make polyclonal antiserum, or antibody-producing cells recovered for fusion (or another immortalization technique) to produce monoclonal antibody-producing cell lines. See, e.g., M. Schreier et al., *Hybridoma Techniques* (1980); Hammerling et al., *Monoclonal Antibodies and T Cell Hybridomas* (1981); Kennett et al., *Monoclonal Antibodies* (1980); U.S. Pat. Nos. 4,341,761; 4,399,121; 4,427,783; 4,444,887. Antiserum produced by the above method will be advantageous in that it will possess a high titer of antibodies which are reactive to all or most HIV-1 isolates. In a similar manner, the screening of hybridomas for non-isolate-specific antibodies will be facilitated by the elimination of some or all of the immunodominant epitopes of the hypervariable regions.

To generate such an antibody response, polypeptides of the present invention are typically formulated with a pharmaceutically acceptable carrier for parenteral administration. The formulation of such compositions, including the concentration of the polypeptide and the selection of the vehicle and other components, is within the skill of the art.

A pharmaceutically acceptable vehicle, suitable for parenteral injection, is usually nontoxic and nontherapeutic. Examples of such vehicles are water, saline, Ringer's solution, dextrose solution, and Hank's solution. Nonaqueous vehicles, such as fixed oils, sesame oil, ethyl oleate, or triglycerides may also be used. Parenteral vehicles may also take the form of suspensions containing viscosity-enhancing agents, such as sodium carboxymethylcellulose, sorbitol, or dextran. The vehicle will also usually contain minor amounts of additives, such as substances that enhance isotonicity and chemical stability. Examples of buffers include phosphate buffer, bicarbonate buffer and tris buffer, while examples of preservatives include thimerosal, m- or c-cresol, formalin and benzyl alcohol. The muteins of the present invention may also be formulated into liposomes for parenteral administration. Standard formulations will either be liquid injectables or solids which can be taken up in a suitable liquid as a suspension or solution for injection. Thus, in a nonliquid formulation, the vehicle may comprise dextrose, human serum albumin, preservatives, etc., to which sterile water or saline could be added prior to administration.

Various adjuvants are known in the art which can also be employed in the vaccine formulations of the present invention; e.g., Freund's adjuvant, avridine, aluminum salts [Al$(OH)_3$AlPO$_4$, Al$_2$(SO$_4$)$_8$], Ca$_3$(PO$_4$)$_2$, saponin, DDA, Plusonics, oil-in-water emulsions (containing, e.g., avridine, dextran sulfate or vitamin E), water-in-oil emulsions (containing, e.g., polysorbate 8), and muramyl peptides (e.g., di- and tripeptides in carriers such as oil-water emulsions or liposomes). The selection of the appropriate adjuvant and its concentration in the vaccine composition is within the skill of the art.

Many protocols for administering the vaccine composition of the present invention to animals are within the skill of the art. The preferred route of administration is parenteral, particularly intramuscular, although administration may also be intravenous. The concentration of the polypeptide antigen in the vaccine composition is selected so that an effective dose is presented to the host mammal (e.g., primate) to elicit antibodies to the polypeptide's epitopes. Within wide limits, the dosage is not believed to be critical. Typically, the vaccine composition is administered in a manner which will deliver between about 1 to about 1,000 ug of the polypeptide antigen in a convenient volume of vehicle (e.g., about 1–10 ml). Preferably, the dosage in a single immunization will deliver from about 1 to about 500 ug of polypeptide antigen, more preferably about 5–10 to about 100–200 ug (e.g., 10–100 ug). It may also be preferred, although optional, to administer a second, booster immunization to the mammal several weeks to several months after the initial immunization. It may be helpful to readminister a booster immunization to the mammal once every several years to maintain high antibody titer.

The following examples are offered for illustrative purposes only, and are not intended to limit the scope of the claims in any way.

designed to be complementary to M13mp8 recombinant templates, of 18 bases in length, and to anneal at a position at least 50 bases away from the mutation locus. Table 2 indicates the oligomers employed for mutagenesis screening and sequencing.

The mutagenesis template contained the entire plasmid pSV7dARV120tPA, which contains the SF2 gp120env gene coupled to the tPA signal sequence (described below). The plasmid was linearized at its unique PstI site and cloned into the unique PstI site of M13mp8.

Table 2

| Mutagenesis Primers | |
| --- | --- |
| D1 | 5' CCACTCTGTGTTACTTTAAATTGCTGCTCTTTCAATATCACCACAAGC 3' |
| D2 | 5' ATAAAAGGAGAAATAAAAAACTGCTGTAACAGATCAGTCATTACACAG 3' |
| D3 | 5' AATGAATCTGTAGCAATTAACTGTTGTAACATTAGTAGAGCACAATGG 3' |
| D4 | 5' GGGGAATTTTTCTACTGTTGTAGAATAAAACAAATTATAAACATGTGG 3' |
| D5 | 5' CTGCTATTAACAAGAGATGGTGGTGAGGTCTTCAGACCTGGAGGAGGA 3' |
| D1 + D2 | 5' CCACTCTGTGTTACTTTAAATTGCTGCTGTAACAGATCAGTCATTACA 3' |
| DNA Sequencing Primers | |
| D1, D2, D1 + D2 | 5' TAATCAGTTTATGGGATC 3' |
| D3 | 5' CTGTTAAATGGCAGTCTA 3' |
| D4, D5 | 5' CAATCCTCAGGAGGGGAC 3' |
| Screening Probes | |
| D1 | 5' TTAAATTGCTGCTCTTTC 3' |
| D2 | 5' AAAAACTGCTGTAACAGA 3' |
| D3 | 5' AATTAACTGTTGTAACATTA 3' |
| D4 | 5' GGGGAATTTTTCTACTGTTGTAGAATAAAACAAATTATAAACATGTGG 3' |
| D5 | 5' ATGGTGGTGAGGTCTT 3' |
| D1 + D2 | 5' CCACTCTGTGTTACTTTAAATTGCTGCTGTAACAGATCAGTCATTACA 3' |

EXAMPLES

EXAMPLE I

The following example describes the construction of DNA sequences encoding HIV-1 SF2 envelope muteins according to the present invention. The hypervariable regions and the corresponding deletions are shown below in Table 1.

TABLE 1

Hypervariable Regions and Deletion Mutants

| Hypervariable Regions | | Corresponding Deletion Mutant(s) | |
| --- | --- | --- | --- |
| V1 | 131 through 154 | D1 | 131 through 154 |
| V2 | 156 through 198 | D2 | 156 through 198 |
| V3 | 292 through 365 | D3 | 300 through 332 |
| V4 | 388 through 414 | D4 | 388 through 414 |
| V5 | 456 through 465 | D5 | 457 through 463 |

DNA encoding sequences for muteins of the present invention were prepared by mutagenesis of a gp120env SF2 gene. Mutagenesis was achieved employing the procedure described by Zoller and Smith, (1983) *Meth. Enzymol.* 100:468–500, modified as described below. Synthetic DNA mutagenesis and sequencing primers (Table 2) were prepared by automated oligonucleotide synthesis on a silica support as described by Urdea et al., (1983) *Proc. Natl. Acad. Sci. USA* 80:7461–7465, using N,N-diisopropyl phosphoramidites. Sequencing primers were designed for sequencing by the dideoxynucleotide chain termination method in bacteriophage M13. Sanger et al., (1977) *Proc. Natl. Acad. Sci. USA* 74:5463. The sequencing primers were Mutagenesis of M13/pSV7dARV120tPA recombinants was performed using purified templates by annealing and extending the appropriate primer with the Klenow fragment of DNA polymerase I. Individual deletion mutants D1, D2, D3 and D5 were obtained utilizing the appropriate mutagenesis primer in a single round of mutagenesis (see Table 2). Deletion mutant D4 was obtained utilizing the appropriate mutagenesis primer with the annealing and elongation reactions performed at 37° C. and in the presence of 125 ug/ml gene 32 protein. Combination deletion mutant D1+D2 was obtained utilizing the appropriate mutagenesis primer using a template derived from deletion mutant D1.

Following transfection of JM101 cells (Zoller and Smith, supra), plaques were grown at a density of 200–1,000/plate and lifted onto filters and screened by hybridization with the appropriate mutagenesis primer or probe (see Table 2).

The DNA sequence of putative positive clones was determined using suitable primers and template preparations. Once the mutagenized locus and flanking segments (i.e., at least 50 bases) were confirmed by DNA sequence analysis, replicative form (RF) DNAs were digested by PstI restriction endonuclease and the entire mutagenized mammalian expression vector pSV7dARV120tPA containing the deletion was recovered. The vector provides an SV40 early promoter and enhancer for expression of SF2 gp120env gene, SV40 polyadenylation site, and an SV40 origin of replication for use of the vector in COS cells.

Following recovery of pSV7dARV120tpa plasmids for wild-type gp120 or for a deletion mutant, the plasmid was digested with SalI to excise the complete gene spliced to the human tPA 5' untranslated sequences and signal sequences. The SalI fragment was subcloned into the unique SalI cloning site of the mammalian cell expression vector pCMV6a. The resulting plasmid was screened to verify the correct orientation of the gene with respect to the promoter and polyadenylation signals, and this plasmid was named pCMV6ARV120tpa for the wild-type gp120 sequences. In cases where the pSV7d vector was not recovered directly as a plasmid, the SalI fragment containing the gene was subcloned from the M13 mutagenesis template clone into pCMV6a.

tions of the various M13-pSV7d- and pCMV6a-based vectors made according to the above protocol.

TABLE 3

| Gene Version | M13 Vector | pSV7d Vector | pCMV6a Vector |
|---|---|---|---|
| Wild-type | M13pSV7d120 | pSV7dARV120tpa | PCMV6ARV120tpa |
| D(1 + 2) | M13PSV7d120D1 + 2 | not made | pCMV6a120D1 + 2 |
| D1 | M13pSV7d120D3 | pSV7d120D1 | PCMV6a120D1 |
| D2 | M13pSV7d120D2 | pSV7d120D2 | pCMV6a120D2 |
| D3 | M13pSV7d120D3 | pSV74120D3 | pCMV6a120D3 |
| D4 | M13pSV7d120D4 | not made | pCMV6al20D4 |
| D6 | M13pSV7d120D5 | not made | pCMV6a120D5 |
| D3 + D4 | M13pSV7d120D3 + D4 | not made | not made |
| D4 + D5 | M13PSV7d120D4 + D | pSV7d12OD4 + D5 | not made |
| D3 + D4 + D5 | not made | PSV7d12OD3 + D4 + D5 | pCMV6a120D3 + D4 + +D5 |
| D(1 − 5) | not made | not made | PCMV6a120D1 − 5 |
| D(1 + 2 + 5) | not made | not made | pCMV6a120D(1 + 2 + 5) |

Combination deletion mutant D4-D5 was obtained utilizing the appropriate D5 mutagenesis primer using a template derived from deletion mutant D4.

Combination deletion mutant pSV7d120D3-D4-D5 was obtained by subcloning the region containing D4-D5 by digestion of M13pSV7d120D4-D5 with MstII and HindIII and insertion of this 334 bp fragment into MstII and HindIII digested pSV7d120D3. The SalI fragment from pSV7d120D3-D4-D5 containing D3-D4-D5 was subcloned into the SalI site of pCMV6a to create pCMV6a120D3-D4-D5.

Combination deletion mutant D1-D2-D5 was obtained by subcloning the region containing D1-D2 by digestion of pCMV6a120D1-D2 with NheI and BglII and insertion of this 540 bp fragment into NheI and BglII digested pCMV6a120D5.

Combination deletion mutant D1-D2-D3-D4-D5 was obtained by subcloning the fragment containing the D1-D2 region by digestion of M13pSV7d120D1-D2 with NheI and BglII and insertion of this 539 bp fragment into NheI and BglII digested pCMV6a120D3-D4-D5.

Expression vector pCMV6a can be regenerated by excising the coding sequence for gp120 from pCMV6ARV120tpa with SalI. The mutein coding sequences described above can all be constructed from the wild-type gp120 coding sequence in pCMV6ARV120tpa as described for pSV7dARV120tpa. Table 3 sets forth the names and delepSV7dARV120tPA (FIG. 3) was constructed as follows. An env gene was modified by in vitro mutagenesis to eliminate any potential transmembrane domains and to provide a stop codon following the processing site between the gp120 and gp41 domains of the gp160 protein. This mutagenesis was accomplished by subcloning the fragment which encodes the env gene from clone pSV7c/env (ATCC Accession No. 67593) by excising with HindIII and XhoI (SF2 clone positions 5582 and 8460) and inserting the 2.8 kb fragment into M13mp19 previously digested with HindIII and SalI. A 37 bp oligonucleotide of the following sequence was used to alter the sequence at the gp120/gp41 processing site at position 7306 to encode 2 stop codons and two restriction endonuclease sites.

5'-GAACATAGCTGTCGACAAGCTTCATCATCTTTTTTCT-3'

The sequence of the wild-type gene and the mutant are shown below:

Wild-type sequence:
```
                                       processing Site
Position:      7288       7294      7300                       7318
Amino acid:    Val Gln Arg Glu Lys Arg Ala Val Gly Ile Val
DNA:           GTG CAG AGA GAA AAA AGA GCA GTG GGA ATA GTA
gp120 mutant:
position:      7288       7294      7300  7306                 7317
Amino Acid:    Val Gln Arg Glu Lys Arg OP OP
DNA:           GTG CAG AGA GAA AAA AGA TGA TGA AGC TTG TCG AC
Restriction site:                                HindIII SalI
```

Following mutagenesis, the gene was engineered for optimal secretion into the medium. A 268 bp XbaI-NdeI fragment containing the heterologous 5' untranslated sequences and signal sequences from human tPA fused to the 5' end of env was excised from the M13 clone M13tpaS.NheIenv described below. This fragment was ligated with a 1363 bp NdeI-SalI fragment encoding the remainder of the gp120 coding region which was isolated from the gp120 mutant (positions 5954 and 7317) described above, and both fragments were inserted into the vector pSV7d (described below) previously digested with XbaI and SalI.

Expression vector pSV7d can be generated by digesting pSV7c/env with BglII and XbaI, and then ligating the digested plasmid with the following linker:

```
     BglII    EcoRI      SmaI    XbaI      BamHI    SalI
5'-GATCTCGAATTCCCCGGGTCTAGAGGATCCGTCGAC
       ABCTTAAGGGGCCCAGATCTCCTAGGCACGTGGATC-5'
```

M13tpaS.NheIenv was constructed as follows. The 5' end of the env coding sequence was modified to accept a heterologous signal sequence known to direct efficient secretion of both the homologous gene (human tissue plasminogen activator) and deletion variants of this gene. van Zonnefeld et al., (1986) *Proc. Natl. Acad. Sci. USA* 83:4670.

A portion of the HIV-1 SF2 gene in a lambda phage (ATCC Accession No. 40143) was excised with SacI and StuI (positions 5555 and 6395) and was subcloned into the vector M13mp19 [Yanisch-Perron et al., (1985) *Gene* 33:103–109] between SacI and SmaI. Oligonucleotide-directed mutagenesis [Zoller et al., (1983) *Meth. Enzymol.* 100:468–500] was used to create an NheI site at the junction of the natural signal peptide and the mature envelope polypeptide using the following oligonucleotide:

5'-GATGCTCTGTTCAGCTAGCGAAAAATTGTGG-3'

This mutagenesis changes cytosine-5867 to guanine and adenine-5868 to cytosine, thereby creating an NheI site and altering the codon for threonine-30 to code for serine.

In parallel, the tPA gene was likewise mutagenized in M13 to place an NheI site near the carboxyl end of the tPA signal peptide. The following sequences show the 5' UT sequences and signal for wild-type tPA leader and for the NheI variant.

Wild-type sequence of the tPA signal:
5' untranslated sequences

The NheI variant of the tPA signal:

5' untranslated sequences

```
AGAGCTGAGATCCTACAGGAGTCCAGGGCTGGAGAGAAAACCTCTGCGAGGAAAGGGAAGGA

GCAAGCCGTGAATTTAAGGGACGCTGTGAAGCAATCATGGATGCAATGAAGAGAGGGCTC
                                    Met Asp Ala Met Lys Arg Gly Leu

TGCTGTGTGCTGCTGCTGTGTGGAGCAGTCTTCGTTTCGCCCAGCGCTAGC
Cys Cys Val Leu Leu Leu Cys Gly Ala Val Phe Val Ser Pro Ser Ala Ser
```

Following mutagenesis and sequence verification, a 174 bp fragment containing 99 bp of 5' untranslated sequence and the signal sequence from tPA was excised from the tPA-containing M13 clone using SalI and NheI and fused to the 559 bp fragment containing the 5' end of the env gene which was excised from the env-containing M13 clone with NheI and HindIII (contributed by the M13 polylinker), and these fragments were subcloned into M13mp18 between SalI and HindIII to give plasmid M13tpaS.NheIenv. The DNA and amino acid sequence of the tPA signal fused to the 5' end of env gene is:

```
  ...     tPA signal        ...                  5869 (amino acid 31 of env)
Phe   Val   Ser   Pro   Ser   Ala   Ser   Glu   Lys   Leu   Trp   Val   Thr   Val
TTC   GTT   TCG   CCC   AGC   GCT   AGC   GAA   AAA   TTG   TGG   GTC   ACA   GTT
                              NheI
```

EXAMPLE II

This example describes the expression of HIV-1 env analogs in mammalian cells.

DNA encoding the complete env gene with the substituted tPA signal sequence was excised from the plasmid pSV7dARV120tpa using the restriction endonuclease SalI and inserted into the unique SalI site of the mammalian cell expression vector pCMV6a, and the resulting plasmid DNA was screened to verify the correct orientation of the gene with respect to the promoter and polyadenylation signals (see Example I). The resulting plasmid, pCMV6ARV120tpa, and the plasmid pSV7dARV120tpa were used to transfect COS-7 cells to test expression and secretion of gp120 into the medium. pCMV6ARV120tpa was at least 50-fold more efficient in expressing gp120 compared with the pSV7dARV120tpa expression plasmid in these cells.

Permanent cell lines were isolated as follows: human kidney 293 cells were plated at a density of 50–70%

```
AGAGCTGACATCCTACAGGAGTCCAGGGCTGGAGAGAAAACCTCTGCGAGGAAAGGGAAGGA

GCAAGCCGTGAATTTAAGGGACGCTGTGAAGCAATCATGGATGCAATGAAGAGAGGGCTC
                                    Met Asp Ala Met Lys Arg Gly Leu

TGCTGTGTGCTGCTGCTGTGTGGAGCAGTCTTCGTTTCGCCCAGCCAGGAAATCCATGCC
Cys Cys Val Leu Leu Leu Cys Gly Ala Val Phe Val Ser Pro Ser Gln Glu Ile His Ala mature tPA
CGATTCAGAAGAGGAGCCAGA TCTTACCAAGTG
Arg Phe Arg Arg Gly Ala Arg  Ser Tyr Gln Val
``` confluency in DME supplemented with glutamine (292 mg/L), sodium pyruvate (110 mg/L), glucose (4.5 g/L), penicillin (1000 U/L), streptomycin (1000 U/L), 3.7 g/L sodium bi-carbonate, and fetal calf serum (10% v/v). Cells were exposed to a calcium phosphate coprecipitate following standard techniques with 10 ug each of the HIV env expression plasmid pCMV6ARV120tpa (wild type or deletion mutant) and a plasmid encoding the selectable marker neomycin-resistance, pSV2neo (Ref), for six hours at 37° C. in a 10% $CO_2$ atmosphere. Cells were washed and exposed to a 3 to 4 minute shock of 15% DMSO or glycerol in HEPES-buffered saline, and growth medium (described above) was replaced for 48 hours. Trypsinized cells were replated at a lower density in 400 ug/ml G418 (Sigma) in DME supplemented as above. Colonies grew to the 100 cell per focus stage in one week to ten days, and these colonies were transferred individually to 96 well plates. Clones were screened for gp120 production by testing the conditioned cell medium using an ELISA described below. Positive clones were scaled up to T75 flasks, aliquots of cells frozen, and cell supernatants were collected for further characterization, e.g. CD4 binding.

Alternatively, CHO dhfr- cells plated at a density of 50–70% confluence were cotransfected by calcium phosphate coprecipitation using 10 ug each of the plasmids pCMV6ARV120tpa (or analogous deletion mutant expression vector) and the selectable marker dhfr encoded in the plasmid pAd-dhfr. Following exposure to the coprecipitate and shock solutions as described above, cells were incubated for 48 hours in Ham's F12 supplemented with glutamine (292 mg/L), sodium pyruvate (110 mg/L), sodium bicarbonate (3.7 g/L), glucose (4.5 g/L), penicillin (1000 U/L), streptomycin (1000 U/L), proline (150 mg/L), and fetal calf serum (10%). Forty-eight hours after transfection, cells were plated at a density of approximately one tenth in DME supplemented as described for F12 above, except that the fetal calf serum was replaced with dialyzed fetal calf serum (10%). Colonies were transferred individually to 96 wells after about two weeks, then screened using the ELISA assay for gp120 secreted into the medium. Positive clones were scaled up as described above.

For detection of gp120 or gp120 hypervariable region deletion mutants in the supernatants of COS, CHO, or 293 cells, conditioned medium was assayed by ELISA specific for gp120 sequences. Pooled HIV-positive human serum inactivated by treatment with psoralen was affinity purified on Staphylococcus Protein A Sepharose by standard techniques. This serum was coated on Immunlon 1 96 well ELISA plates at a concentration of 5 ug/ml in PBS and plates were incubated 12 hours to two months at 4° C. Following incubation, plates were washed as described for the titration ELISA (Example IV), and samples and standards (including purified recombinant HIV-1 gp120env from yeast) were applied to the plate in two-fold dilution series using the dilution buffer described for the titration ELISA. The range of the assay is 100 ng/ml to 200 pg/ml. Samples were incubated for 12 hours at 4 C. Samples were aspirated and plates were washed as above. Samples were then incubated with an appropriate dilution of rabbit serum from rabbits immunized with recombinant SF2 gp120env analog (usually 1:100 dilution of Protein A Sepharose affinity-purified serum in dilution solution) for 1 hour at 37° C., followed by washing. Color development was with ABTS, as described for the titration ELISA. Plates were read as described, and the amount of gp120 in each sample was determined by using a standard curve derived from the standard on the same plate. The assay was verified by showing that HIV-infected HUT 78 cells (infected cell lysate) gave a positive signal, while uninfected cell lysates were negative.

EXAMPLE III

This example describes the recombinant production of muteins in yeast hosts according to the present invention.

The starting plasmid used for the construction of yeast expression vectors was plasmid pJS150. This plasmid is similar to plasmid pBS24.1/SOD-SF2env4–5 (U.S. Ser. No. 138,894, filed 24 Dec. 1987, supra), and has had the yeast promoter and HIV coding sequences located between the unique BamHI and SalI sites replaced with a yeast ADH2/GAPDH promoter and a portion of an Zairan HIV-1 isolate envelope coding sequence. In addition, the NheI restriction site located in the plasmid vector portion was destroyed by cutting with NheI, nuclease S1 treatment, followed by ligation.

Plasmid pJS150 was digested with restriction enzyme NcoI, which cuts just after the translation initiation ATG codon downstream from the ADH2/GAPDH promoter (as well as at other sites in the vector). The fragments were ligated to an NcoI/NheI adaptor having the sequence:

After ligation, the DNA sequences were digested with BamHI and NheI to generate a 1.2 kb BamHI-NheI fragment containing the ADH2/GAPDH promoter and an NheI sticky end immediately downstream. This DNA fragment was isolated by gel electrophoresis and is referred to as Fragment A.

A second digest was performed by cutting plasmid pJS150 with BamHI and SalI to generate a 13 kb linear DNA vector. This DNA fragment was also purified by gel electrophoresis, and is referred to as Fragment B. A third DNA fragment containing a coding sequence for gp120 D3 mutein was isolated from pCMV6a120D3 (Table 3 of Example I) by digestion with NheI and SalI. The approximate 1.2 kb coding fragment was then gel isolated, and is referred to as Fragment C.

The three fragments (A, B and C) were then ligated together, and the resulting ligation mix was used to transform E. coli strain HB101 to ampicillin resistance. A plasmid containing all three fragments in the proper orientation is shown in FIG. 5. This D3 yeast expression vector was designated pHL15. Expression vectors for additional muteins were also constructed by cloning the mutein-encoding sequence of the pCMV6a-based vectors (Example I, Table 3) into NheI/SalI-digested pHL15, thereby replacing the D3 coding sequence. The deletions and corresponding vectors that were made are shown in Table 4.

TABLE 4

| Deletion | Vector |
| --- | --- |
| D1 | pHL24 |
| D2 | pHL25 |
| D3 | pHL15 |
| D4 | pHL26 |
| D5 | pHL27 |
| D1 + D2 | pHL22 |
| D3 + D4 + D5 | pHL21 |
| D1 through D5 | pHL20 |

The yeast expression vectors described above were used to transform Saccharomyces cerivisiae strain JSC308

(ATCC accession No. 20879, deposited 5 May 1988) to uarcil prototrophy. Uracil prototrophs were then streaked onto leucine selective plates to isolate leucine prototrophs (as a result of plamsmid amplification in vivo). Expression of the deletion muteins was achieved by growing a seed culture of the leucine prototrophs in leucine selective medium and then diluting it into approximately 10 liters of a rich medium containing yeast extract, peptone, and glucose. Either 2% or 4% glucose was used as the carbon source in the media, whichever appeared optimal.

Muteins were purified as follows. Frozen yeast cells were thawed and suspended in 1 volume of lysis buffer, 0.001M PMSF, 0.001M EDTA, 0.15M NaCl, 0.05M Tris-HCl pH 8.0), and 1 volume of acid-washed glass beads added. Cells were broken in a noncontinuous system using a 300 ml glass unit of Dyno-mill at 3000 rpm for 10 min. the jacket was kept cool by a −20° C. ethylene glycol solution. Glass beads are decanted by letting the mixture set for 3 min on ice. The cell extract was recovered and centrifuged at 18,000 rpm (39,200×g) for 35 min. The supernatant was discarded and the precipitate (pellet 1) further treated as indicated below.

Pellet 1 was resuspended in 4 volumes of Tris-HCl buffer (0.01M Tris-HCl, pH 8.0, 0.01M NaCl, 0.001M PMSF, 1 ug/ml pepstatin, 0.001M EDTA, 0.1% SDS) and extracted for 1 hr at 4° C. with agitation. The solution was centrifuged at 6,300×g for 15 min. The insoluble fraction (pellet 2) was resuspended in 4 volumes (360 ml) of PBS (per liter: 0.2 g KCl, 0.2 g $KH_2PO_4$, 8.0 g NaCl, 2.9 g $Na_2HPO_4.12H_2O$), 0.1% SDS, 0.001M EDTA, 0.001M PMSF, 1 ug/ml pepstatin, and centrifuged at 6,300×g for 15 min. This pellet (pellet 3), was suspended in 4 volumes of PBS, 0.2% SDS, 0.001M EDTA, 0.001M PMSF, 1 ug/ml pepstatin and extracted for 12 hr at 4° C. with agitation on a tube rocker. The solution was then centrifuged at 6,300×g for 15 min. The soluble fraction was recovered for further purification as indicated below. (The pellet can be reextracted by resuspending it in 4 volumes of 2.3% SDS, 5% beta-mercaptoethanol, and boiling for 5 min. After boiling, the solution is centrifuged at 6,300×g for 15 min. The soluble fraction is recovered for further purification.) The soluble fraction was concentrated by precipitation with 30% ammonium sulfate at 4° C. The pellet (pellet 4) was then resuspended in 2.3% SDS, 5% beta-mercaptoethanol, and chromatographed on an ACA 34 or ACA 54 (LKB Products) gel filtration column (depending on the size of the mutein). The column was equilibrated with PBS, 0.1% SDS, at room temperature. Chromatography was developed in the same solution with a flow rate of 0.3 ml/min. If needed, pooled fractions were concentrated by vacuum dialysis on Spectrapor #2 (MW cutoff 12–14K).

EXAMPLE IV

This example describes an immunoassay for anti-HIV antibodies employing HIV-1 env analogs.

Immulon-1 96 well immunoassay plates are coated with gp120 antigen by dispensing 100 ul per well of a 2 ug per ml purified antigen produced in yeast (Env SF2 wild type, env HTLV wild type, env Zr6 wild type, env SF2-D3, env SF2-D1-D2, env SF2-D3-D4-D5, env SF2-D1-D2-D3-D4-D5 in 50 mM borate pH 9.2 at 4° C. for at least 12 hours and less than 60 days. The coating is aspirated from the plate, and the plate is washed six times by dunking in a solution of 0.137M NaCl (0.8%), 0.05% Triton-X 100. The plate is patted dry, and 100 ul per well of 100 mM sodium phosphate, 0.1% casein, 1 mM EDTA, 1% Triton-X 100, 0.5M NaCl, 0.01% thimerosol pH 7.5 (dilution solution) is added.

Sera to be tested are prepared for analysis by diluting 5 ul test serum (from HIV-positive humans and normal humans, or from immunized animals) in 500 ul of the dilution solution above (1/100 dilution v/v). The solution in the top wells is aspirated off and 150 ul of diluted test serum is added. Using a multichannel pipettor set at 50 ul, dilutions down each column are carried out, taking 50 ul each time (⅓ dilution v/v). The plates are then incubated 1 hour at 37° C. with the plate wrapped in plastic wrap. The samples are then aspirated off and washed 6 times as above. Then, 100 ul per well of goat anti-human IgG conjugated to horseradish peroxidase (Tago 2733 Lot 330102) diluted 1/2000 in dilution solution is added. The plates are then incubated 30 minutes at 37° C. covered in plastic wrap. The solution is again aspirated off and washed 6 times as above. 100 ul per well of color developing solution is added [100 ul ABTS stock (15 mg/ml 2,2'-A zino-di-(3 ethylbenzthiazolene sulfonic acid), Sigma A-1888, in water, stored in the dark at 4° C.) plus 3.3 ul 30% hydrogen peroxide in 10 ml citrate buffer (10.5 g citric acid per liter water, pH to 4.0 with 6M NaOH)]. The ABTS solution is made no more than 10 minutes prior to use, and the solution should be made with citrate buffer at room temperature. Plates in plastic wrap are incubated at 37° for 30 minutes in the dark. The reaction was stopped with 50 ul per well of 10% sodium dodecyl sulfate.

Plates were read at 415 nm with a reference wavelength at 600 nm. Titers are determined as follows from the raw data: absorbance (linear axis) is plotted vs. dilution factor (log axis) on semilog paper or computer program.

Included in the test sera are standard reference sera as positive controls. For titration of human sera, HIV-positive serum 20058 from the Interstate panel was used; for goat sera, a goat serum developed by immunization with envSF2 wild-type, reference 02GT097.2 was used; and for titration of guinea pig sera, a standard reference guinea pig serum was used, likewise obtained by immunization with envSF2 wild-type, reference +Gp sera 1935/77. From the values obtained on the ELISA reader, an absorbance value was chosen that is half-maximal ($OD_{50}$) (between 0.5 and 0.7) in the linear portion of the standard curve (positive control), for each plate. The average titer for the standards on the plate were determined. The average titer was divided by the "Reference Titer" for that species and antigen plate, and the resulting number is the "correction factor". The test sera titers were divided by the correction factor to yield the adjusted, normalized titers.

Figures 2, 3, 4, 5, 6, 6C:
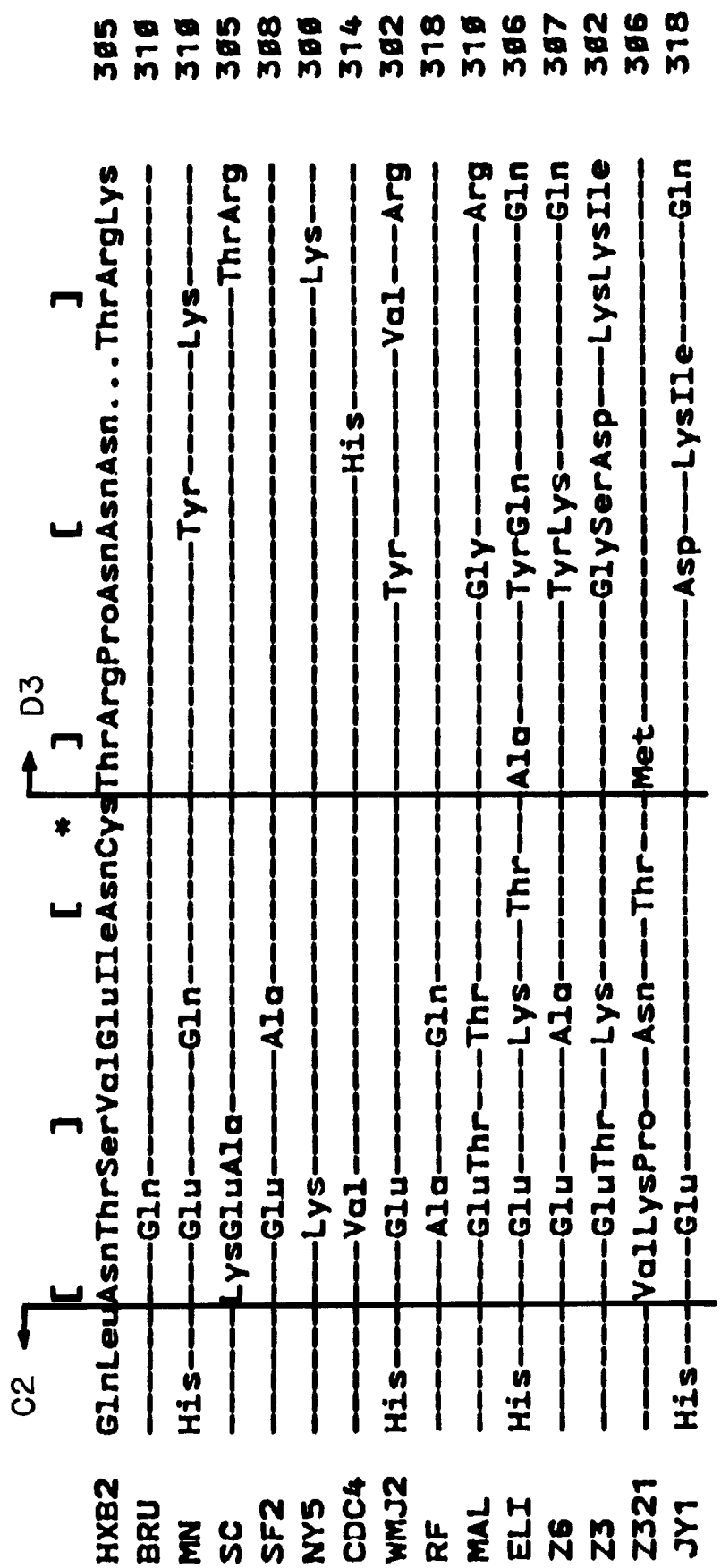
FIG. 6 contains graphs showing the result of an ELISA testing the reactivity of HIV-1 envelope muteins of the present invention and controls against a North American serum panel.

A panel of selected human sera was tested to determine their titers on all of the recombinant antigens, including the deletion muteins env SF2 D1-2, env SF2-D-3, env SF2-D1-2-3-4-5, and env SF2-D3-4-5. Results are shown in FIG. 6 (North American serum panel) and FIG. 7 (African serum panel). The graphs show that for these serum samples, the recombinant antigen env SF2-D1-2 is as efficient or more efficient in detecting sera as is env SF2 wild-type. Recombinant antigens env SF2-D3, env SF2-D3-4-5 and env SF2-D1-2-3-4-5 are as efficient as env HTLVIII wild-type or env Zr6 wild-type.

EXAMPLE V

This example describes the immunization of mammals with recombinant hypervariable region muteins and the detection of immune responses in these animals in response to these injections. Recombinant env antigens purified from yeast were used to generate anti-HIV antibodies in experimental animals of very high titer. In both goats and guinea pigs, the titers of the resulting sera were at a similar level, whether the immunogen was env SF2 wild-type or an env SF2 hypervariable mutein.

Immunization of Guinea Pigs

In order to test if guinea pigs imunized with env SF2 muteins derived from yeast were capable of generating a strong immune response, these animals were immunized with several muteins and control antigens.

For each antigen, six Hartley guinea pigs were immunized in the footpad with 50 ug each antigen mixed with 50 ug adjuvant (see below) at three week intervals with a total of seven injections. Blood samples were taken at the time of each injection (prebleed at injection 1), and the serum was monitored by titration in the ELISA described above in Example IV for the production of antibodies directed against the immunizing antigen and against heterologous env antigens.

Antigens:
Env SF2-D3
Env SF2-D-1-2-3-4-5
Env SF2-D3-4-5
Env HTLVIII wild-type

Adjuvant:
Muramyl-tripeptide-phosphatidyl ethanolamine in squalene-Tween.

Vaccine:
Mix adjuvant with correct volume of 10X Squalene-Tween (carrier) to make a final concentration of 1X (4% squalene, 0.008% Tween-20), antigen, and PBS to make the correct volume and dose (50 ug each of antigen and adjuvant per animal in 100 ul injection volume per animal. Warm the mixture for 5 min at 45° C. Pass the warm mixture in and out of a 23 ga. needle six times, taking care to avoid introducing air into the mixture. Inject into the animals immediately. If the injection procedure takes more than 5 min, remix the emulsion by shaking by hand every few minutes.

Control:
Control animals receive the adjuvant in carrier.

Figures 2, 3, 4, 5, 6, 7, 8, 9, 9A:
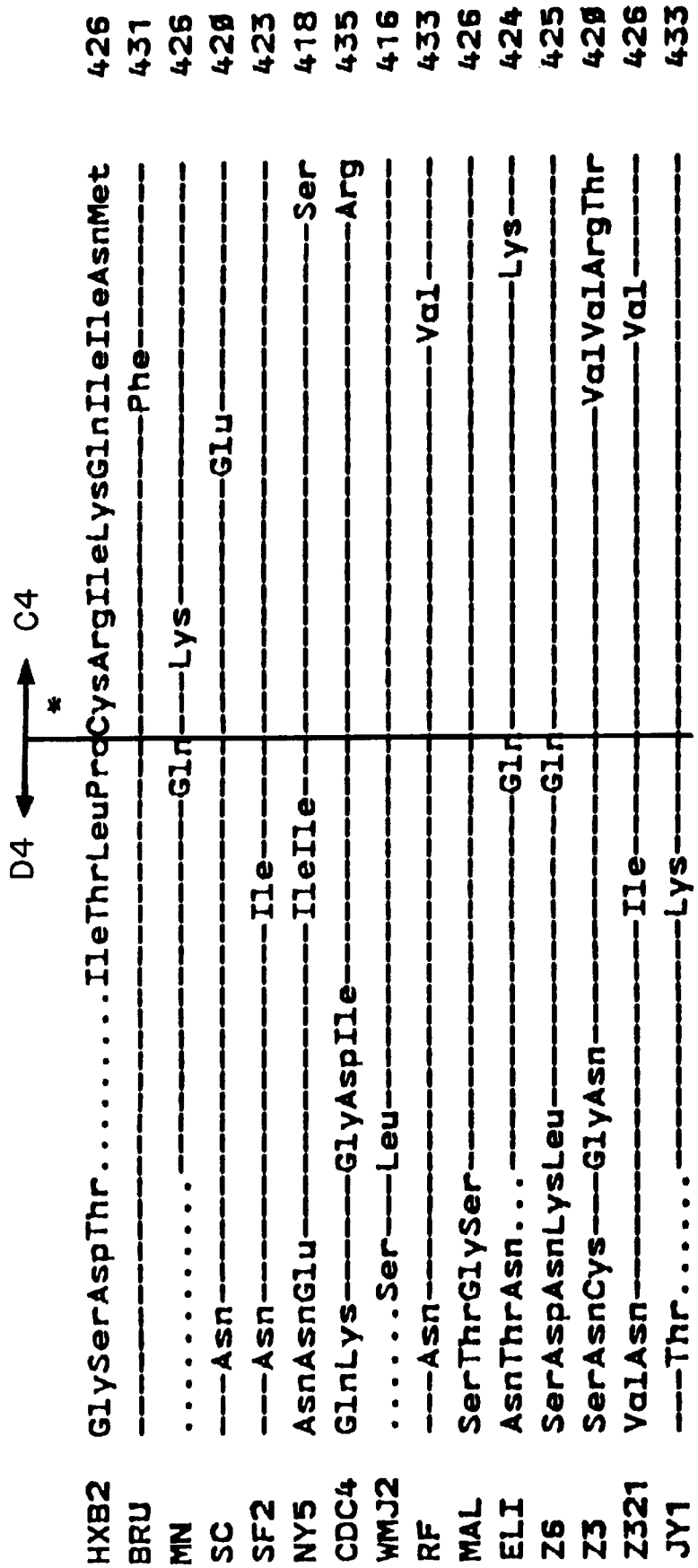
FIG. 7 contains graphs showing the result of an ELISA testing the reactivity of HIV-1 envelope muteins of the present invention and controls against an African serum panel.
FIG. 8 shows the results of an ELISA using sera from guinea pigs immunized with envelope muteins according to the present invention or various controls.
FIG. 9 shows the results of an ELISA using sera from goats immunized with envelope muteins according to the present invention or various controls.
Figure 3:
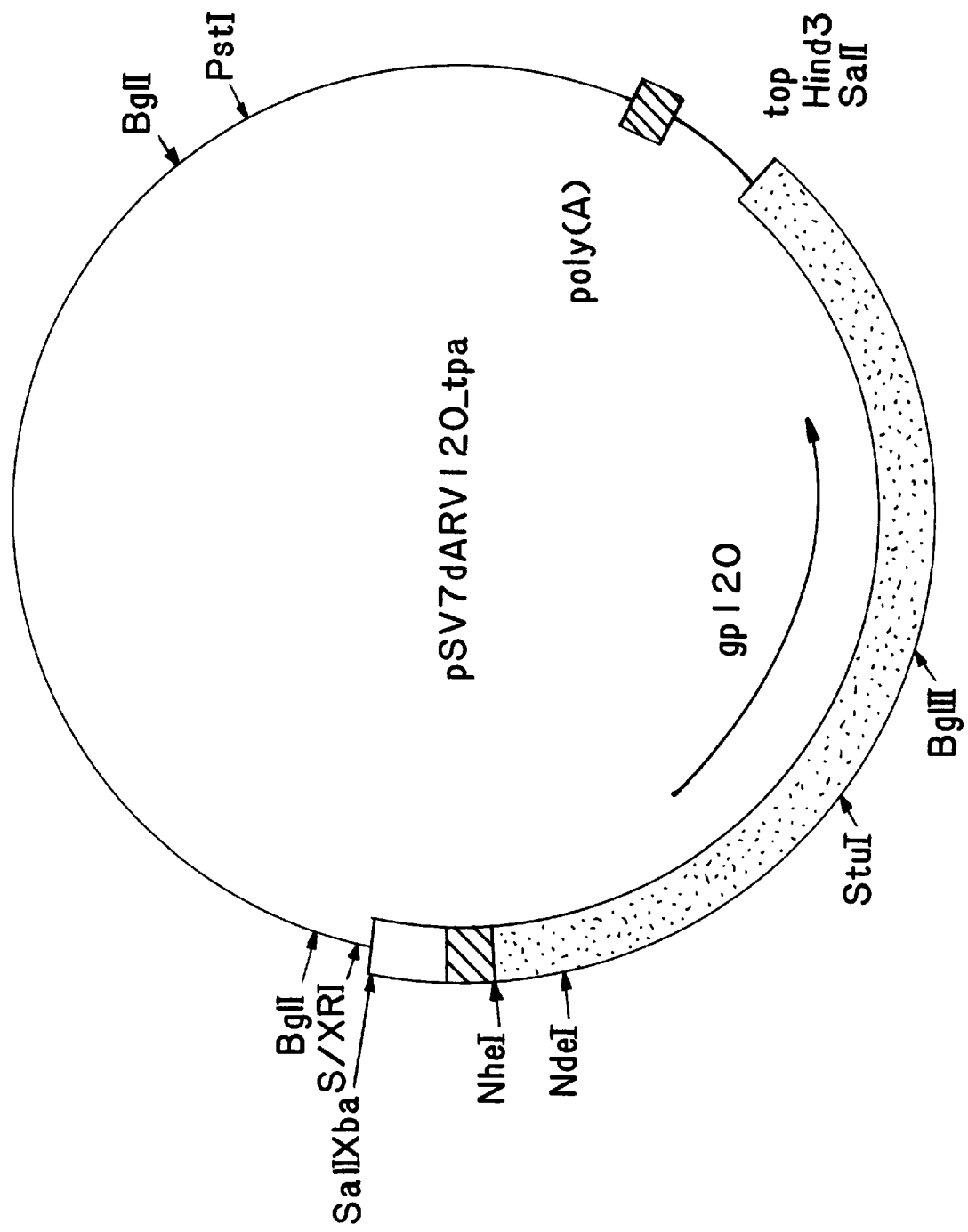
Figure 4:
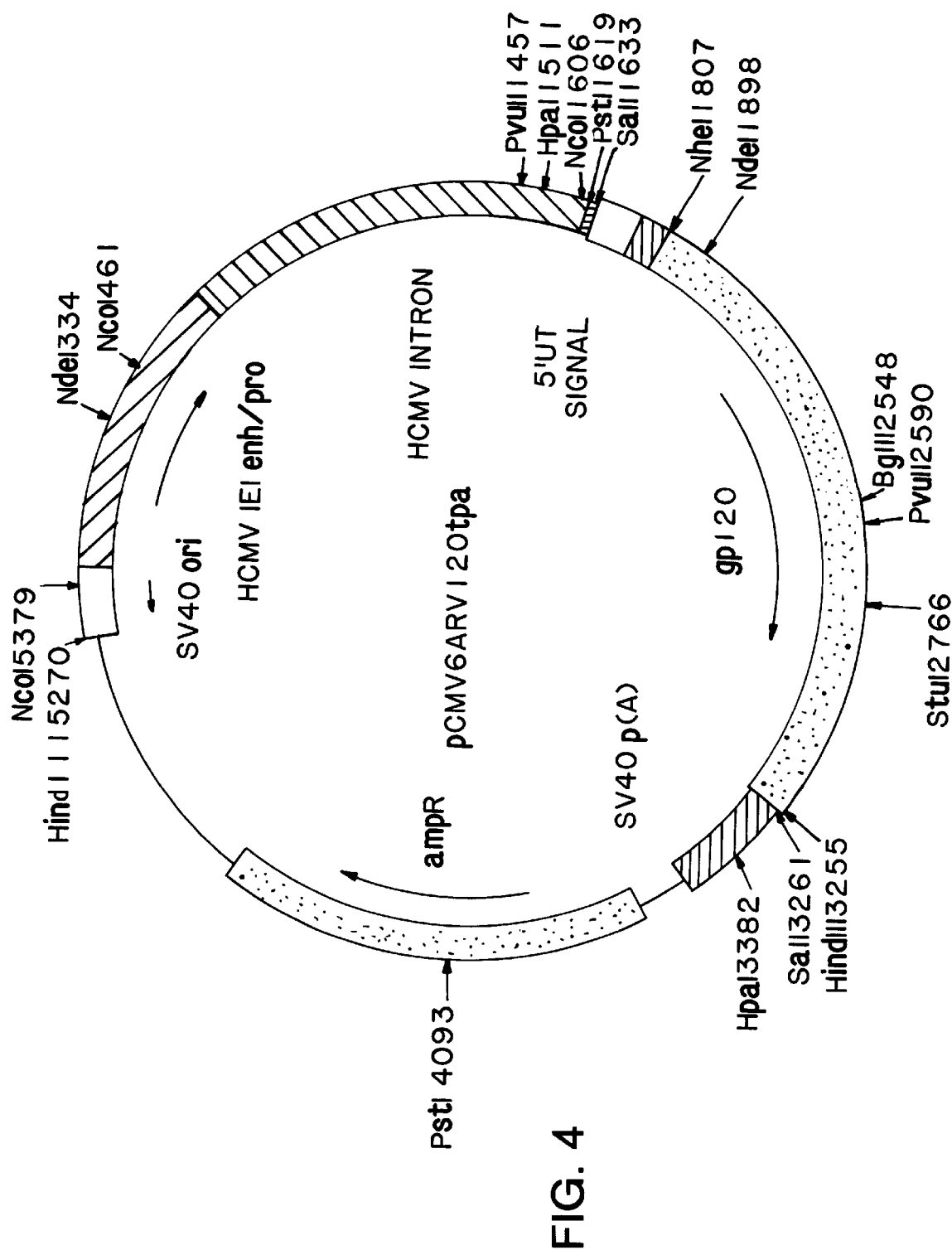
Figure 5:
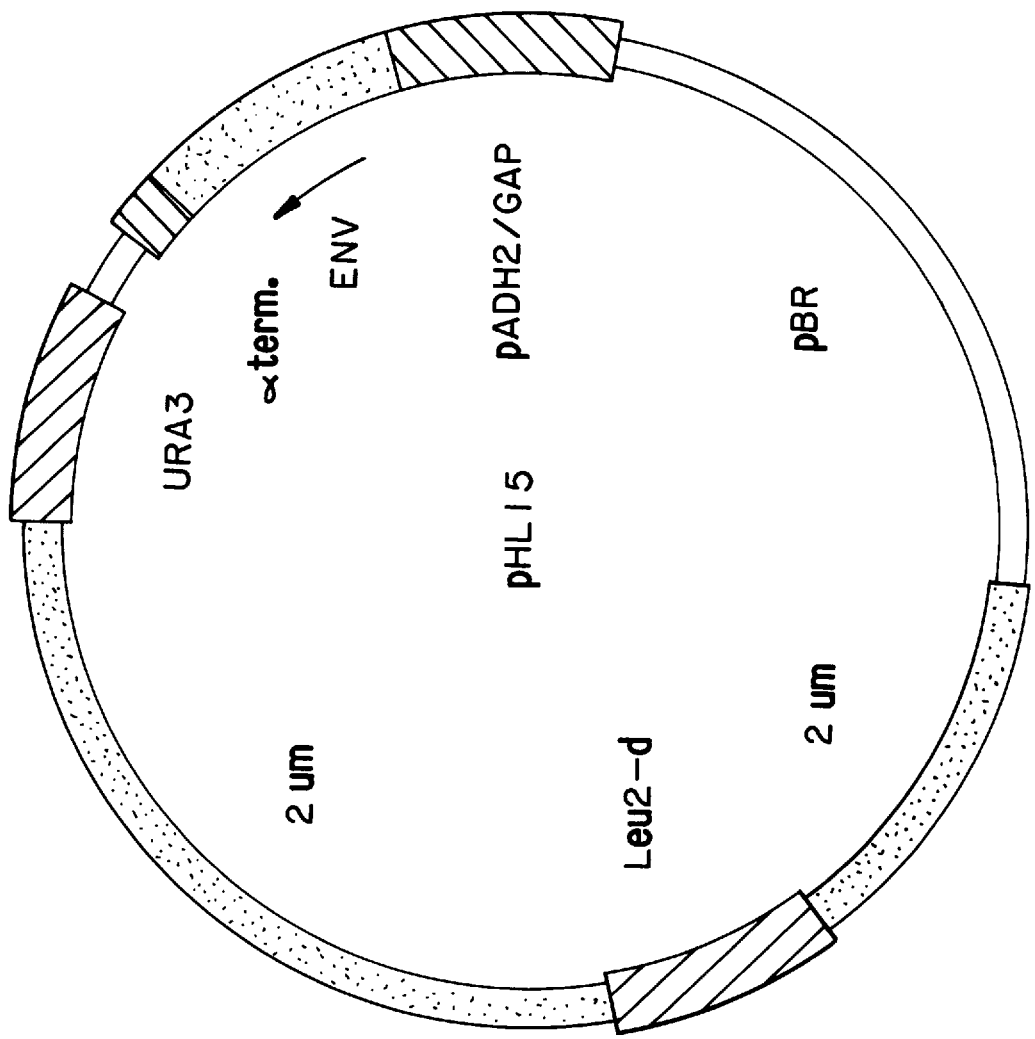
Figures 7A, 7B:
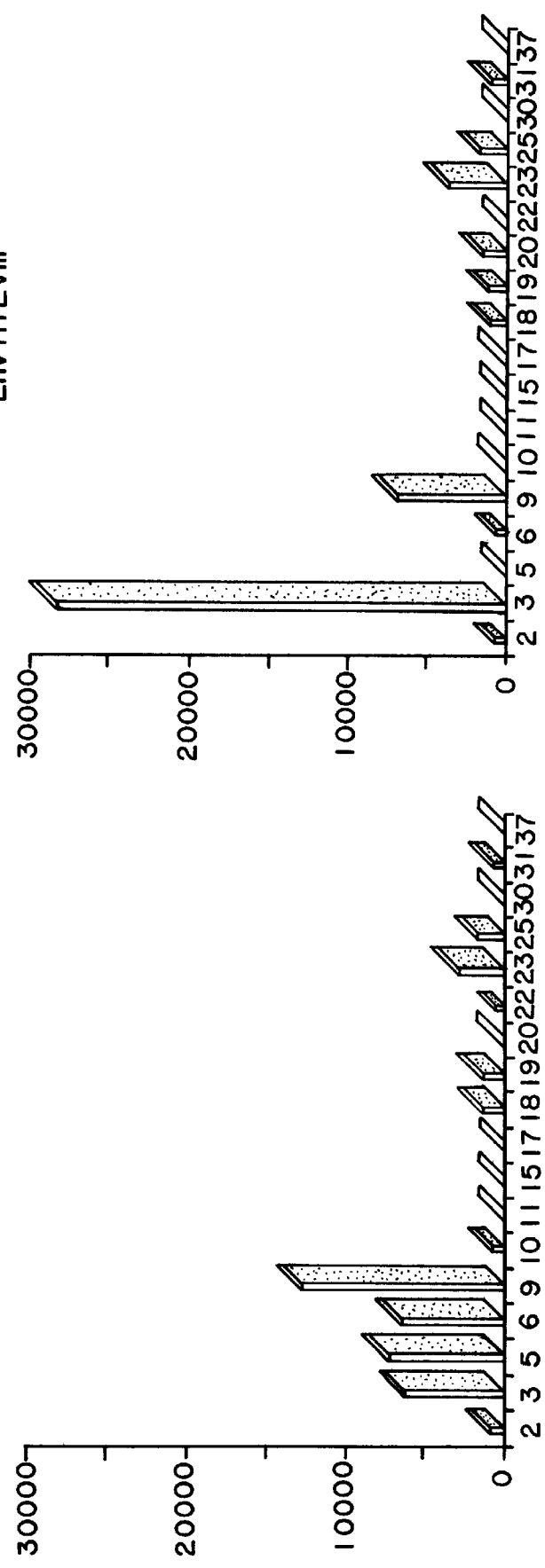
Figure 7C:
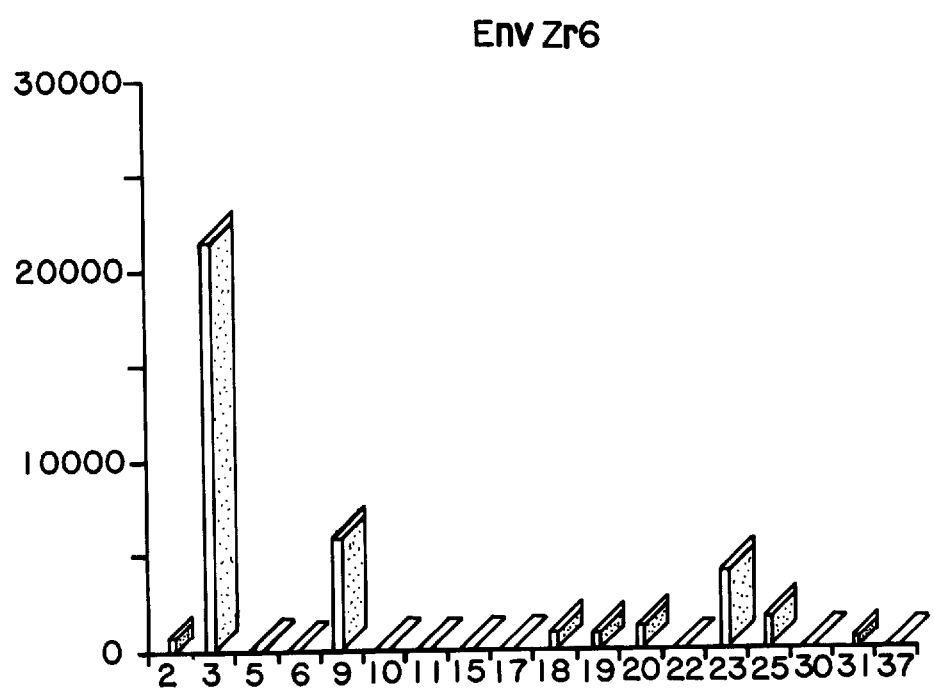
Figure 7E:
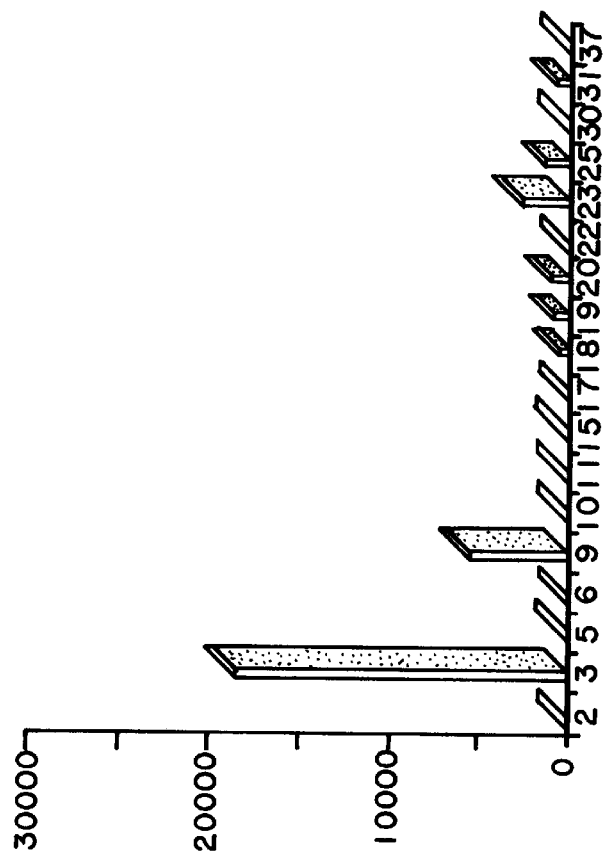
Figure 7D:
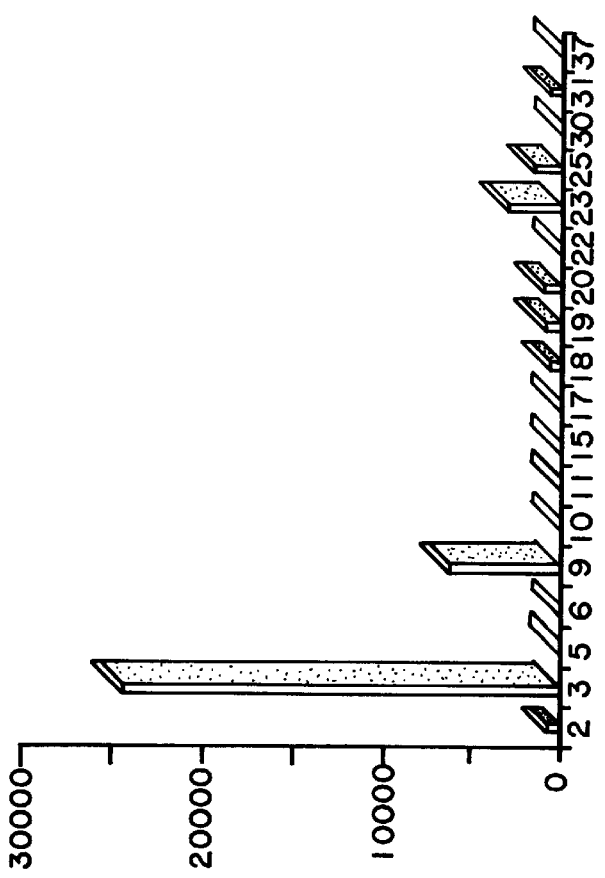
Figure 9C:
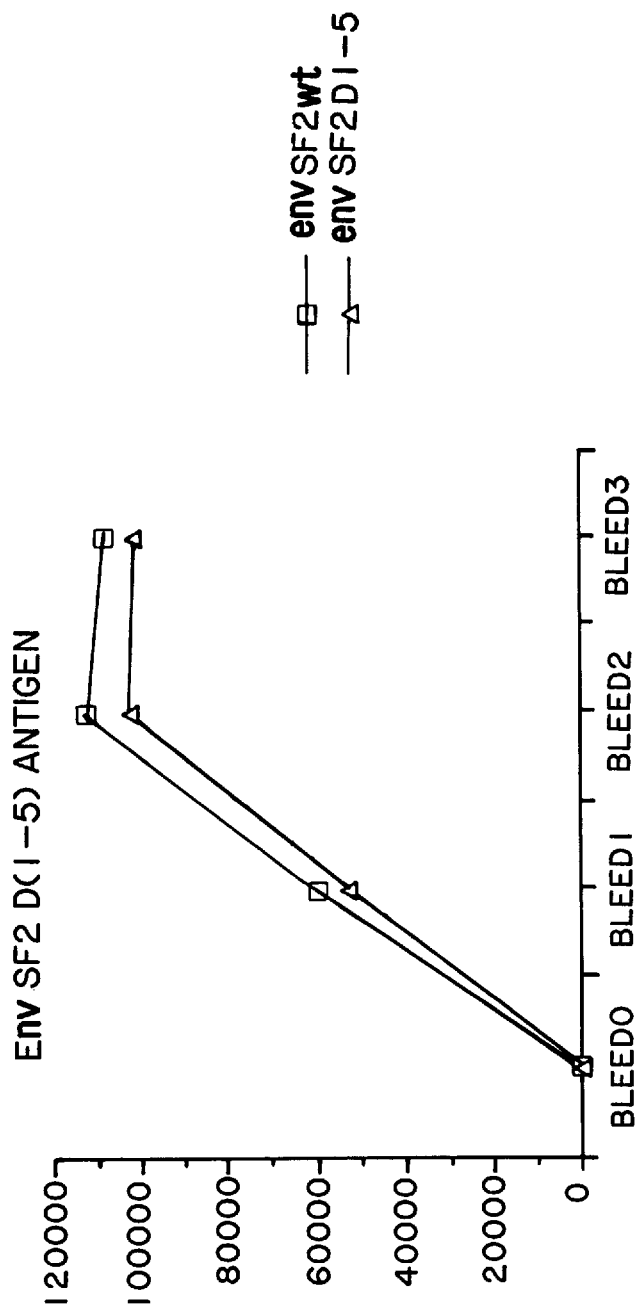

Results:
The results of the ELISA are shown in FIG. 8. As can be seen, the muteins of the present invention are as effective as wild-type envelope in generating high antibody titers. A standard virus neutralization assay was also conducted the guinea pig sera. The results are shown in Table 5. The data show that deletion mutants of the present invention can generate significant levels of neutralizing antibodies.

TABLE 5

Virus Neutralization by Guinea Pig Sera

| Antigen | Animal Number | ELISA Titer/ env SF2 | Neutralization Titer HIV-SF2 |
|---|---|---|---|
| Env SF2 D3 | 2477 | 280,000 | 50 |
| (COOH half) | 2476 | 221,000 | 500 |
| | 2479 | 274,000 | 250 |
| | 2480 | 190,000 | 100 |
| | 2481 | 115,000 | <20 |
| Env 5F2 D3 | 2471 | 45,000 | >500 |
| | 2473 | 57,000 | <20 |
| | 2474 | 116,000 | <20 |
| | 2475 | 26,000 | <20 |
| | 2476 | 16,000 | <500 |
| Env 5F2 D(3-5) | 2489 | 342,000 | 500 |
| (full length) | 2490 | 88,000 | 30 |
| | 2491 | 131,000 | 45 |
| | 2492 | 83,000 | 25 |
| | 2494 | 253,000 | 30 |
| Env 5F2 D(1-5) | 2483 | 131,000 | <20 |
| | 2484 | 71,000 | <20 |

TABLE 5-continued

Virus Neutralization by Guinea Pig Sera

| Antigen | Animal Number | ELISA Titer/ env SF2 | Neutralization Titer HIV-SF2 |
|---|---|---|---|
| | 2485 | 60,000 | <20 |
| | 2486 | 54,000 | <20 |
| | 2487 | 100,000 | <20 |
| | 2488 | 133,000 | <20 |
| Env HTLVIII | 2523 | 23,000 | <20 |
| | 2524 | 37,000 | <20 |
| | 2525 | 52,000 | <20 |
| | 2526 | 23,000 | <20 |
| | 2527 | 70,000 | <20 |
| | 2528 | 14,000 | <20 |

Immunization of Goats

In order to test if goats immunized with env SF2 muteins derived from yeast were capable of generating a strong immune response, these animals were immunized with several muteins and control antigens.

For each antigen, two goats were immunized intramuscularly with 1 mg each primary injection (complete Freund's adjuvant) and 0.5 mg each booster injection (incomplete Freund's adjuvant) at three week intervals with a total of six injections. Blood samples were taken at the time of each injection (prebleed at injection 1), and the sera were monitored by titration in the ELISA assay described above in Example IV for the production of anti-bodies directed against the immunizing antigen and against heterologous env antigens.

| Antigens: | Env SF2-D3 | Lot 3064/1a |
| | Env SF2-D1-a2-3-4-5 | Lot 3064/5a |
| | Env HTLVIII wild-type | Lot 3064/15a |

Adjuvant: Complete Freund's and incomplete Freund's.

Vaccine: Mix 0.5 ml antigen (1 mg) with 0.5 ml complete Freund's. Emulsify by standard procedures and inject. For boosters, mix 0.5 ml antigen (0.5 mg) with 0.5 ml incomplete Freund's. Emulsify and inject.

Control: Control animals receive the adjuvant in carrier.

Results: The results of the ELISA are shown in FIG. 9. As can be seen, the muteins of the present invention are at least as effective as wild-type polypeptides in antibody titer levels generated.

Deposit of Biological Materials

Vectors pCMV6ARV120tpa and pHL15, both in E. coli HB101, were deposited with the American Type Culture Collection (ATCC), 12301 Parklawn Drive, Rockville, Md., USA, on 13 September 1988, and will be maintained under the provisions of the Budapest Treaty on the Deposit of Microorganisms. The accession number for the pCMV6ARV120tpa deposit is 67792, and the accession number for the pHL15 deposit is 67793.

These deposits are provided for the convenience of those skilled in the art, and are neither an admission that such deposits are required to practice the present invention, nor that equivalent embodiments are beyond the skill of the art in view of the present disclosure. The availability of these deposits is not a grant of any license (e.g., to make, use or sell the deposited materials) under this or any other patent. The nucleic acid sequences of the deposited materials are incorporated in the present disclosure by reference and are controlling if in conflict with any sequence described herein.

Although the foregoing invention has been described in some detail by way of illustration and example, it will be obvious that changes and modifications may be practiced within the scope of the apended claims.

I claim:

1. A DNA sequence encoding a human immunodeficiency virus type 1 (HIV-1) envelope mutein having the structure $C_1$-$V_1$-$V_2$-$C_2$-$V_3$-$C_3$-$V_4$-$C_4$-$V_5$-$C_5$ wherein said mutein retains the conserved domains $C_1$-$C_5$ and has a deletion of at least one of the hypervariable domains $V_1$-$V_5$.

2. The DNA sequence of claim 1 wherein said HIV-1 encoded mutein is strain SF2.

3. The DNA sequence of claim 1 in which at least hypervariable region $V_1$ is deleted from the encoded mutein.

4. The DNA sequence of claim 1 in which at least hypervariable region $V_2$ is deleted from the encoded mutein.

5. The DNA sequence of claim 1 in which at least hypervariable region $V_3$ is deleted from the encoded mutein.

6. The DNA sequence of claim 1 in which at least hypervariable region $V_4$ is deleted from the encoded mutein.

7. The DNA sequence of claim 1 in which at least hypervariable region $V_5$ is deleted from the encoded mutein.

8. The DNA sequence of claim 1 in which $V_1$ is deleted from the encoded mutein.

9. The DNA sequence of claim 1 in which $V_2$ is deleted from the encoded mutein.

10. The DNA sequence of claim 1 in which $V_3$ is deleted from the encoded mutein.

11. The DNA sequence of claim 1 in which $V_4$ is deleted from the encoded mutein.

12. The DNA sequence of claim 1 in which $V_5$ is deleted from the encoded mutein.

13. The DNA sequence of claim 1 in which $V_1$ and $V_2$ are deleted from the encoded mutein.

14. The DNA sequence of claim 1 in which $V_3$, $V_4$ and $V_5$ are deleted from the encoded mutein.

15. The DNA sequence of claim 1 in which $V_1$ through $V_5$ is deleted from the encoded mutein.

* * * * *